United States Patent
Adam et al.

(10) Patent No.: US 8,716,037 B2
(45) Date of Patent: May 6, 2014

(54) MEASUREMENT OF CMOS DEVICE CHANNEL STRAIN BY X-RAY DIFFRACTION

(75) Inventors: Thomas N. Adam, Slingerlands, NY (US); Stephen W. Bedell, Wappingers Falls, NY (US); Eric C. Harley, LaGrangeville, NY (US); Judson R. Holt, Wappingers Falls, NY (US); Anita Madan, Danbury, CT (US); Conal E. Murray, Yorktown Heights, NY (US); Teresa L. Pinto, Walkill, NY (US)

(73) Assignee: International Business Machines Corporation, Armonk, NY (US)

( * ) Notice: Subject to any disclaimer, the term of this patent is extended or adjusted under 35 U.S.C. 154(b) by 552 days.

(21) Appl. No.: 12/967,323

(22) Filed: Dec. 14, 2010

(65) Prior Publication Data
US 2012/0146050 A1 Jun. 14, 2012

(51) Int. Cl.
*G01R 31/26* (2006.01)
*H01L 21/66* (2006.01)

(52) U.S. Cl.
USPC ..................................... 438/14; 257/E21.529

(58) Field of Classification Search
CPC ............................................... G01N 2223/607
USPC ......................... 438/14; 356/32; 257/E21.529
See application file for complete search history.

(56) References Cited

U.S. PATENT DOCUMENTS

| | | | |
|---|---|---|---|
| 5,442,676 A | 8/1995 | Fewster | |
| 5,576,223 A | 11/1996 | Zeininger et al. | |
| 6,744,501 B2 | 6/2004 | Klose | |
| 7,166,838 B1 | 1/2007 | Janik | |
| 7,521,265 B2 | 4/2009 | Yokokawa | |
| 7,600,916 B2 | 10/2009 | Yokhin et al. | |
| 7,653,174 B2 | 1/2010 | Mazor et al. | |
| 7,741,200 B2 | 6/2010 | Cho et al. | |
| 2006/0228850 A1* | 10/2006 | Tsai et al. | 438/219 |
| 2008/0012073 A1 | 1/2008 | Frohberg et al. | |
| 2008/0078996 A1 | 4/2008 | Usuda | |
| 2009/0309160 A1 | 12/2009 | Cohen et al. | |

\* cited by examiner

*Primary Examiner* — Daniel Luke
(74) *Attorney, Agent, or Firm* — Scully, Scott, Murphy & Presser, P.C.

(57) ABSTRACT

A direct measurement of lattice spacing by X-ray diffraction is performed on a periodic array of unit structures provided on a substrate including semiconductor devices. Each unit structure includes a single crystalline strained material region and at least one stress-generating material region. For example, the single crystalline strained material region may be a structure simulating a channel of a field effect transistor, and the at least one stress-generating material region may be a single crystalline semiconductor region in epitaxial alignment with the single crystalline strained material region. The direct measurement can be performed in-situ at various processing states to provide in-line monitoring of the strain in field effect transistors in actual semiconductor devices.

15 Claims, 16 Drawing Sheets

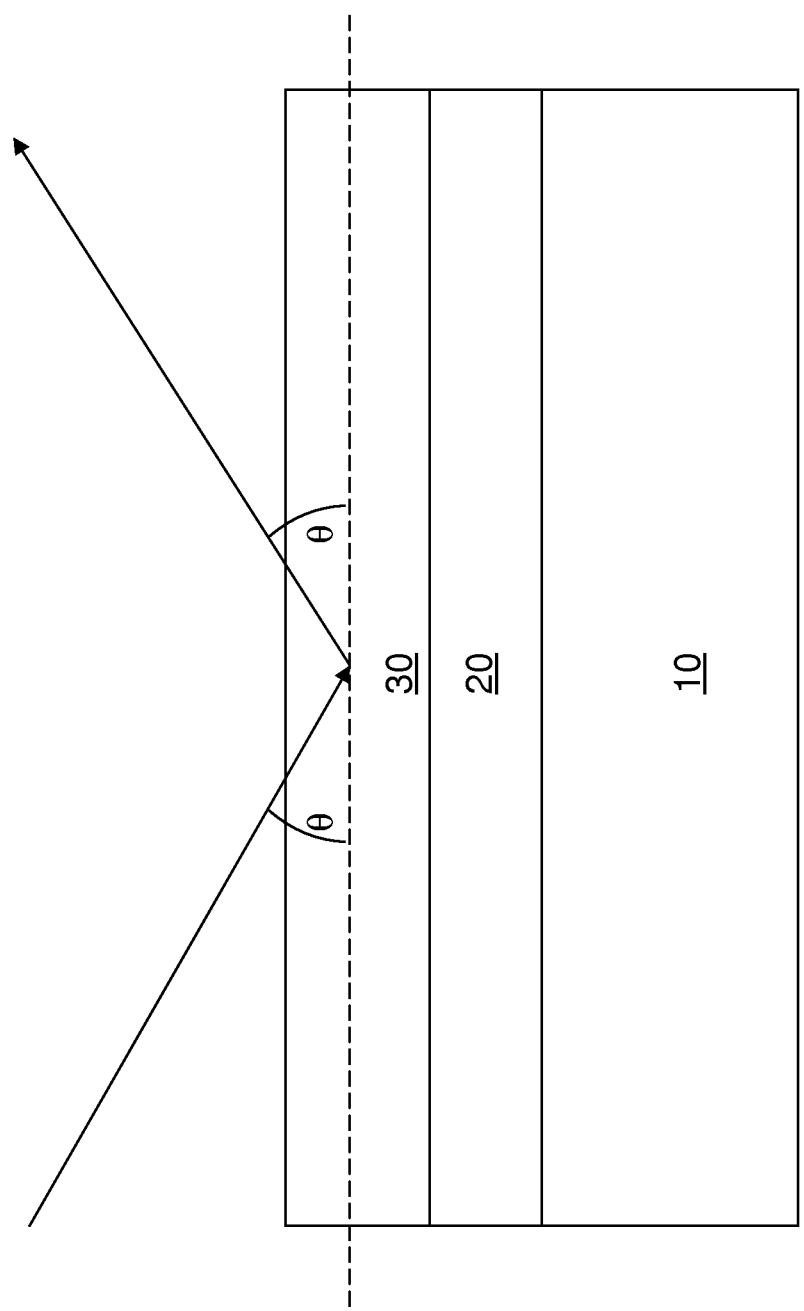

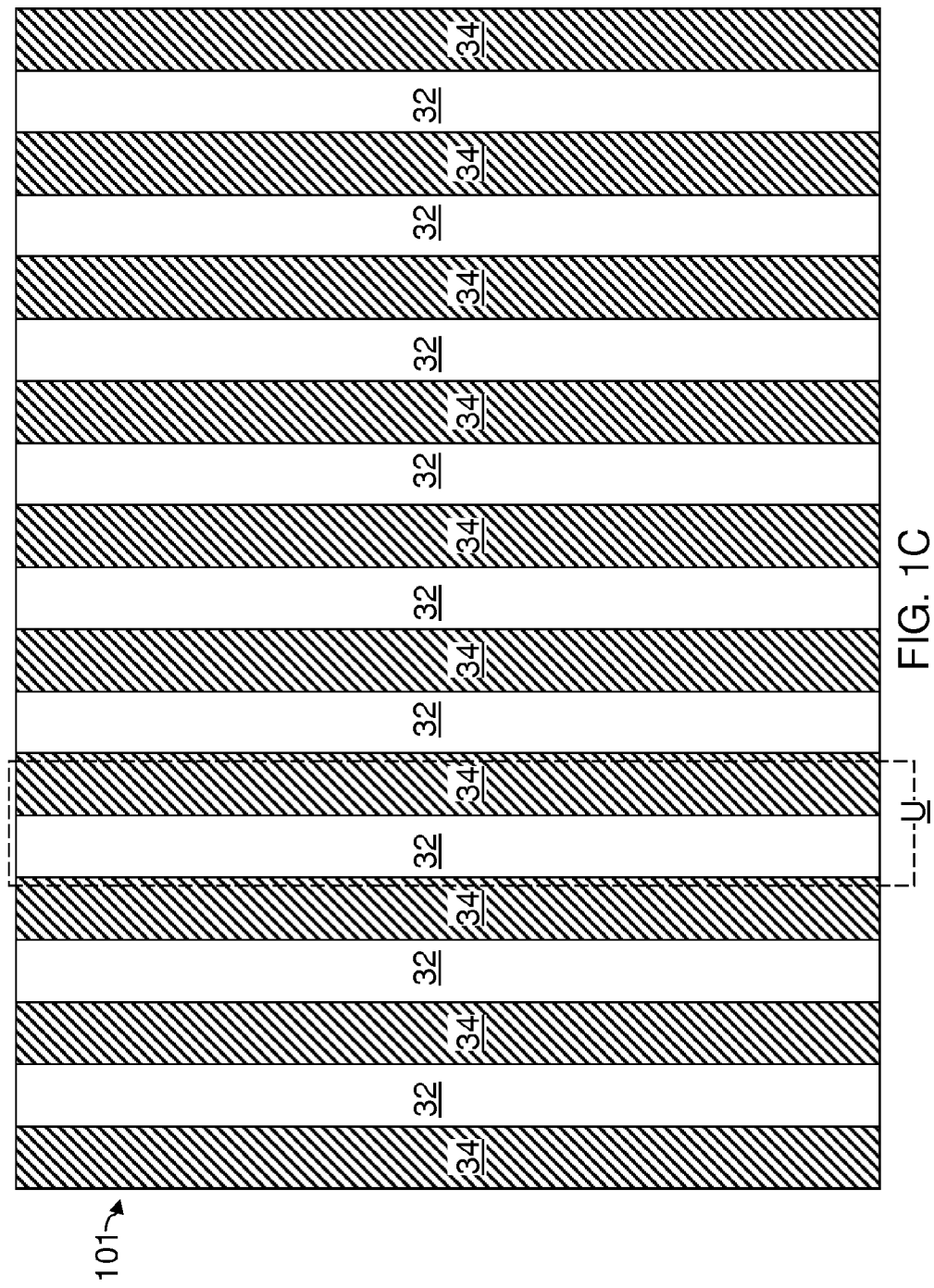

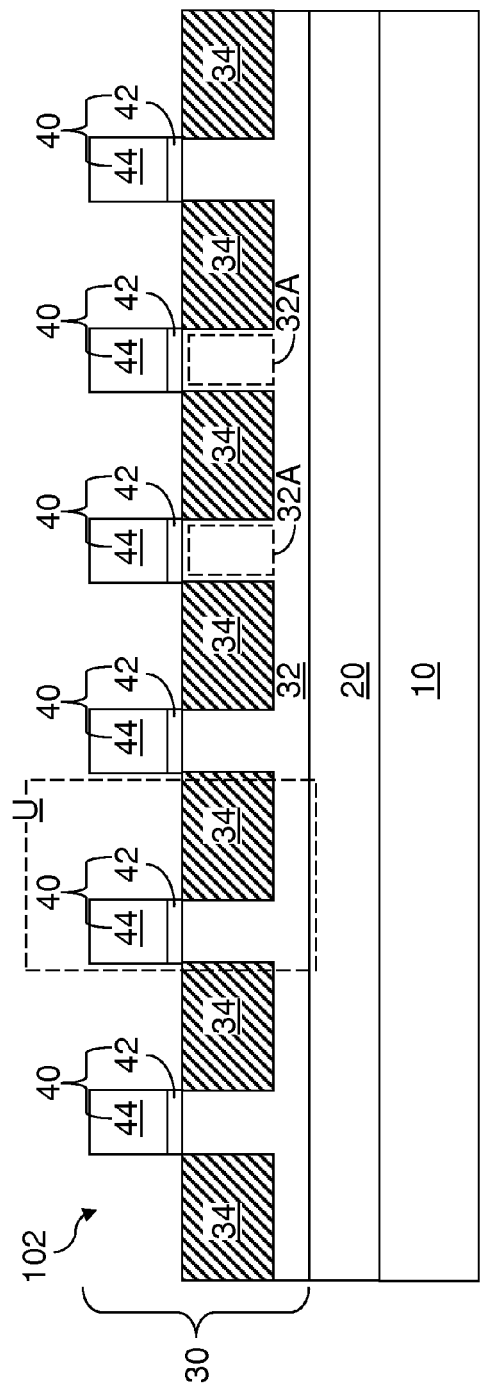
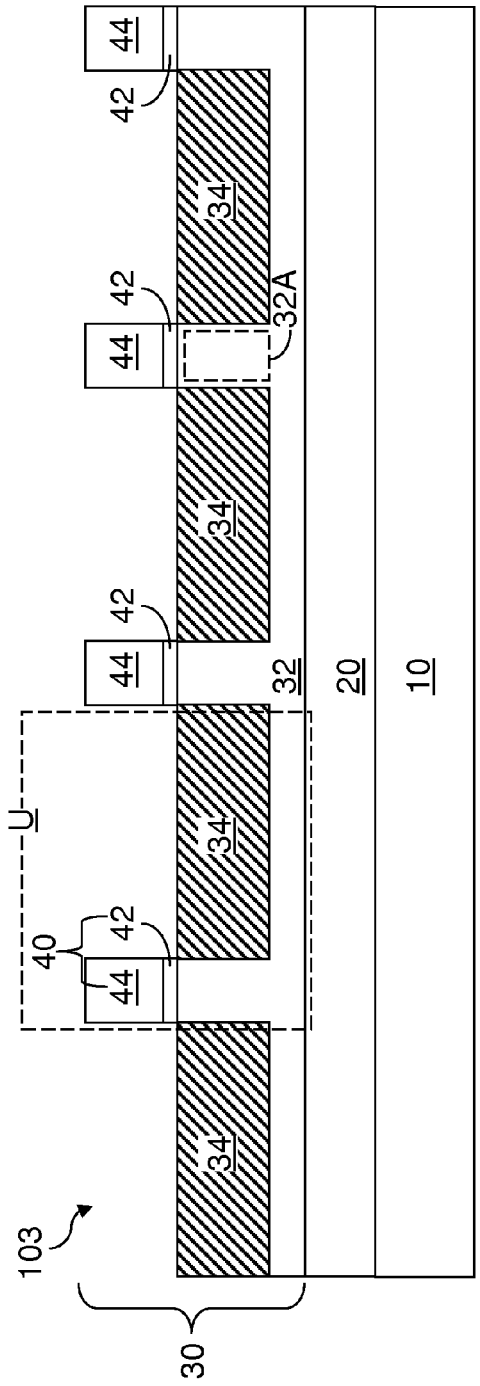

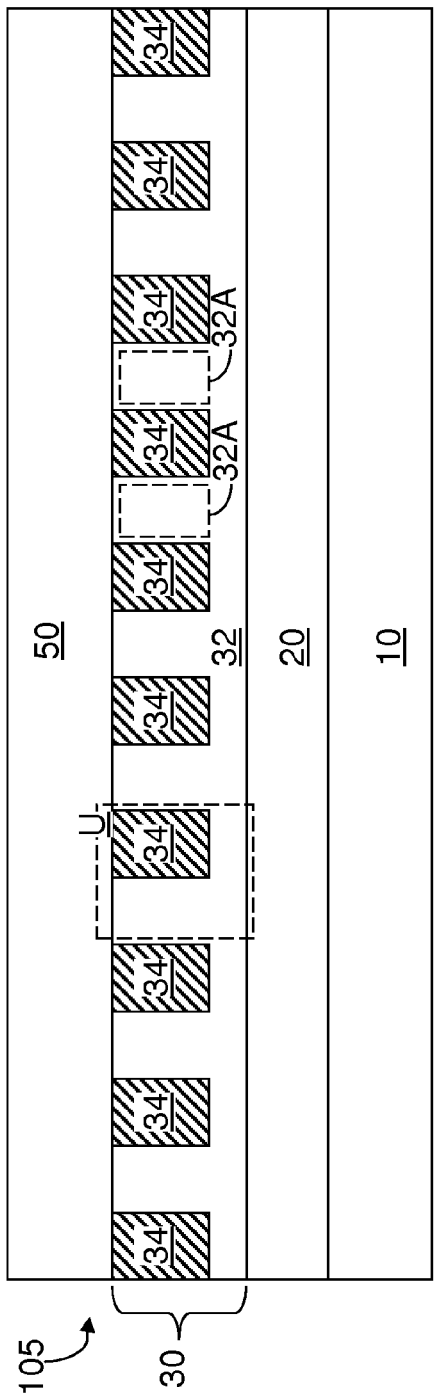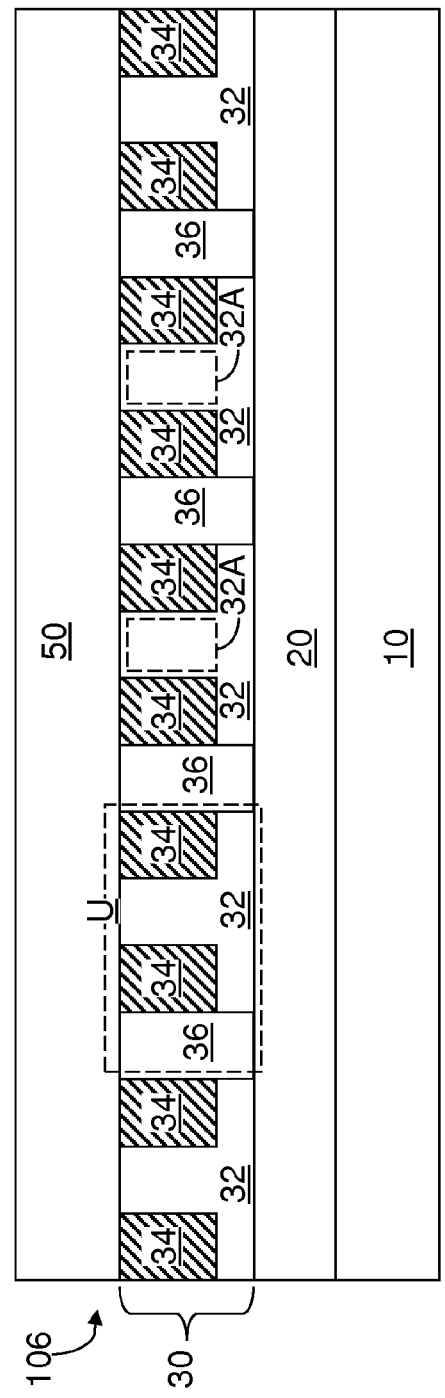

MEASUREMENT OF CMOS DEVICE CHANNEL STRAIN BY X-RAY DIFFRACTION

BACKGROUND

The present disclosure generally relates to a method of measurement, and specifically to a method of measuring the strain in a CMOS device with stress-generating elements using X-ray diffraction (XRD), and structures for effecting the same.

When stress is applied to the channel of a semiconductor transistor, the applied stress and the resulting strain on the semiconductor structure within the channel affects the band gap structure (i.e., breaks the degeneracy of the band structure) and changes the effective mass of carriers. The effect of the stress depends on the crystallographic orientation of the plane of the channel, the direction of the channel within the crystallographic orientation, and the direction of the applied stress. Under stress applied to the channel of the MOSFET, the mobility of carriers, and as a consequence, the transconductance and the on-current of the transistor are altered from their original values for an unstressed semiconductor.

The effect of uniaxial stress, i.e., a stress applied along one crystallographic orientation, on the performance of semiconductor devices has been extensively studied in the semiconductor industry. For a p-type MOSFET, i.e., a PMOSFET (or a "PFET" in short) that utilizes a silicon channel or silicon-germanium alloy channel, the mobility of minority carriers in the channel (which are holes in this case) increases under longitudinal compressive stress along the direction of the channel, i.e., the direction of the movement of holes or the direction connecting the drain to the source. Conversely, for an n-type MOSFET, i.e., an NMOSFET (or an "NFET" in short) that utilizes a silicon channel or a silicon-germanium alloy channel, the mobility of minority carriers in the channel (which are electrons in this case) increases under longitudinal tensile stress along the direction of the channel, i.e., the direction of the movement of electrons or the direction connecting the drain to the source.

When a material is compressed in one direction, the material tends to expand in the other two directions perpendicular to the direction of compression. Conversely, if the material is stretched rather than compressed, the material tends to contract in the directions transverse to the direction of stretching. This phenomenon is called the Poisson effect, and is characterized by Poisson's ratio v. The Poisson's ratio is the ratio of the fraction (or percent) of expansion in one direction divided by the fraction (or percent) of compression in another direction, for small values of these changes. Thus, strain along one direction is invariably coupled with strain along other directions in a single crystalline material, and an accurate measurement of strain in one direction not only provides data on the strain and stress in the crystallographic direction along which the measurement is taken, but also significantly contributes to accurate estimation of the stress and strain along all other crystallographic orientations.

BRIEF SUMMARY

In this disclosure, a direct measurement of lattice spacing by X-ray diffraction is performed on a periodic array of unit structures that is provided on a substrate including semiconductor devices. Each unit structure includes a single crystalline strained material region and at least one stress-generating material region. For example, the single crystalline strained material region may be a structure simulating a channel of a field effect transistor, and the at least one stress-generating material region may be a single crystalline semiconductor region in epitaxial alignment with the single crystalline strained material region. The direct measurement can be taken in-situ at various processing states to provide in-line monitoring of the strain in field effect transistors in actual semiconductor devices.

According to an aspect of the present disclosure, a method of monitoring strain on a single crystalline structure with stress-generating elements is provided. The method includes: providing a periodic array of unit structures on a substrate, wherein each of the unit structures includes a single crystalline strained material region and at least one stress-generating material region that applies stress to the single crystalline strained material region; performing an X-ray scan on the periodic array of unit structures to generate an X-ray scan spectrum; locating a Bragg peak of a material of the single crystalline strained material region in the X-ray scan spectrum; and determining strain in a direction in single crystalline strained material regions in the periodic array of unit structures based on a location of the Bragg peak in the X-ray scan spectrum.

According to another aspect of the present disclosure, a semiconductor structure is provided. The semiconductor structure includes: a periodic array of unit structures on a substrate, wherein each of the unit structures includes a single crystalline strained material region, at least one stress-generating material region that applies stress to the single crystalline strained material region, and a single crystalline unstrained material region, wherein the periodic array of unit structures is not contacted by any structure configured to apply electrical current through any portion of the periodic array of unit structures; and a semiconductor device on the substrate including another single crystalline strained material region and at least another stress-generating material region that applies stress to the other single crystalline strained material region, wherein the semiconductor device is configured to flow electrical current through the single crystalline strained material region.

BRIEF DESCRIPTION OF THE SEVERAL VIEWS OF THE DRAWINGS

FIG. 1A is a schematic view illustrating X-ray diffraction geometry according to an embodiment of the present disclosure.

FIG. 1C is a see-through top-down view of the first exemplary structure according to an embodiment of the present disclosure.

FIG. 6A is a vertical cross-sectional view of a second exemplary structure according to an embodiment of the present disclosure.

FIG. 6B is a vertical cross-sectional view of a third exemplary structure according to an embodiment of the present disclosure.

FIG. 10 is a vertical cross-sectional view of a fifth exemplary structure according to an embodiment of the present disclosure.

FIG. 11 is a vertical cross-sectional view of a sixth exemplary structure according to an embodiment of the present disclosure.

DETAILED DESCRIPTION

Figure 1B:
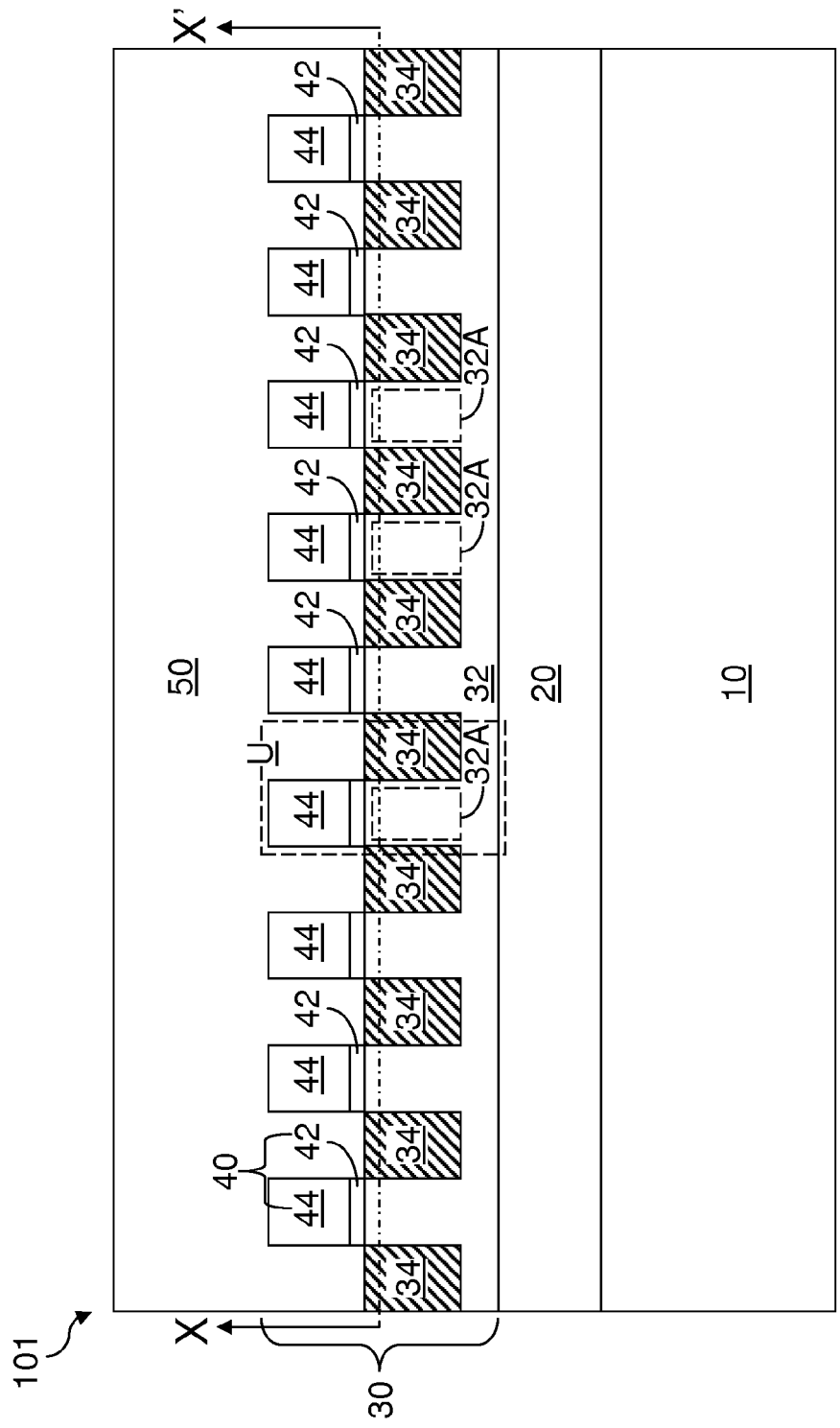
FIG. 1B is a vertical cross-sectional view of a first exemplary structure according to an embodiment of the present disclosure.

As stated above, the present disclosure relates to a method of measurement, and specifically to a method of in-line X-ray diffraction (XRD) monitoring of strain generated by stress-generating elements, and structures for effecting the same, which are now described in detail with accompanying figures. It is noted that like reference numerals refer to like elements across different embodiments. The drawings are not necessarily drawn to scale.

Referring to FIG. 1A, X-ray diffraction (XRD) geometry employed for the purposes of the present disclosure is schematically illustrated. A sample for X-ray diffraction includes a substrate containing a periodic array of unit structures. The periodic array of unit structures can be located in a periodic-structure-containing layer 30 which forms a portion of the substrate. For example, the substrate may be a semiconductor substrate including at least one semiconductor material layer. In case the substrate is a semiconductor substrate, the substrate can be a semiconductor-on-insulator (SOI) substrate including a handle substrate 10, a buried insulator layer 20, and a top semiconductor layer (not separately shown) that is included in the periodic-structure-containing layer 30. Alternately, the semiconductor substrate can be a bulk semiconductor substrate in which a semiconductor layer includes a portion of the periodic-structure-containing layer 30 and extends to one side, e.g., a bottom side, of the semiconductor substrate.

The periodic-structure-containing layer 30 can include a single crystalline semiconductor material layer. The single crystalline semiconductor material layer can be contiguous throughout a lower portion of the periodic-structure-containing layer 30, and can include silicon, germanium, carbon, a silicon-germanium, a silicon-carbon alloy, or a silicon-germanium-carbon alloy. In one embodiment, the single crystalline semiconductor material layer can be a single crystalline silicon layer.

The periodic-structure-containing layer 30 includes a periodic array of unit structures (not shown separately). An X-ray diffraction scan can be performed on the substrate including the periodic-structure-containing layer 30 to determine the distance between adjacent atomic layers in various portions of the periodic-structure-containing layer 30. Specifically, the X-ray diffraction scan can be performed to determine the location of Bragg peaks, which occurs at an angle at which parallel atomic layers provide a constructive interference pattern among scattered X-ray beam paths in a 2θ X-ray scan. A 2θ X-ray scan is an X-ray scan in which the angle 2θ, formed between the direction an incident X-ray beam and the direction from a sample to a detector, is varied during the X-ray scan. In some cases, the angle between a set parallel atomic planes and the incident beam can be maintained at θ, and the angle between the set of parallel atomic planes and the direction of the detector can be can be maintained at θ as well.

Referring to FIG. 1B, a first exemplary structure 101 according to an embodiment of the present disclosure includes a stack, from bottom to top, of a handle substrate 10, a buried insulator layer 20, a periodic-structure-containing layer 30, and at least one dielectric material layer 50. The periodic-structure-containing layer 30 can include a single crystalline semiconductor layer 32 and a plurality of stress-generating material regions 34. In general, the periodic-structure-containing layer 30 includes a periodic array of unit structures U. Each of the unit structures U includes a single crystalline strained material region 32A and at least one stress-generating material region 34 that applies stress to the single crystalline strained material region.

Each single crystalline strained material region 32A can be of integral construction with a single crystalline unstrained material region, which is the complement of the single crystalline strained material region 32A in a portion of the single crystalline semiconductor layer 32 in each unit structure U. Each single crystalline unstrained material region 32A is a portion of the single crystalline semiconductor layer 32 below the bottom surfaces of the stress-generating material regions 34. The entirety of each single crystalline strained material region 32A and the entirety of each single crystalline unstrained material region can be of integral construction, epitaxially aligned to one another, and collectively constitute the single crystalline semiconductor layer 32. Each single crystalline strained material region 32A and each single crystalline unstrained material region can include the same single crystalline semiconductor material, which is strained in the single crystalline strained material regions 32A and not strained in the single crystalline unstrained material regions.

The periodic-structure-containing layer 30 can further include a stack 40 of a dielectric material portion 42 and a conductive material portion 44. The stack 40 can have the same composition and dimensions as a gate stack (not shown)

of a field effect transistor including a gate dielectric (not shown) and a gate electrode (not shown). Specifically, the dielectric material portion 42 can have the same composition and thickness as, and can be formed in the same processing step as, a gate dielectric of a field effect transistor. The conductive material portion 44 can have the same composition and thickness as, and can be formed in the same processing step as, a gate electrode of a field effect transistor.

Additional structures that can be formed on functional semiconductor devices (not shown) can be formed on the periodic-structure-containing layer 30. For example, dielectric spacers (not shown) having the same composition and thickness as a dielectric gate spacer on a gate stack of a field effect transistor can be formed on the stack 40 of the periodic-structure-containing layer 30 at the same processing step as the formation of the dielectric gate spacer. The periodic-structure-containing layer 30 need not include any functional semiconductor device. Instead, the periodic-structure-containing layer 30 can include non-functional semiconductor structures that do not pass electrical currents. However, the dimensions of each single crystalline strained material region 32A, stack 40, and stress-generating material region 34 can be selected to match corresponding dimensions in semiconductor devices such as field effect transistors. For example, the width of each single crystalline strained material region 32A can be selected to be equal to the distance between embedded source and drain regions of a field effect transistor, and the composition and dimensions of each stress-generating material region 34 can be selected to match the composition and corresponding dimensions of the embedded source and drain regions of the field effect transistor. Further, the same single crystalline semiconductor layer 32 can be employed to form the functional semiconductor devices such as field effect transistors.

At least one dielectric material layer 50 may, or may not be, present over the periodic-structure-containing layer depending on embodiments and depending on processing steps after which the substrate including the periodic-structure-containing layer 30 is tested to have the strain within each single crystalline strained material region 32A measured. Unit structure simulates nested functional semiconductor devices (not shown) that can be formed in a different region of the substrate including the periodic array of unit structures 30.

The lateral extent of the first exemplary structure 101 is selected to be greater than the beam size of the X-ray diffraction apparatus to be employed to analyze the lattice parameters of single crystalline material portions in the periodic-structure-containing layer 30. For example, the lateral extent of the first exemplary structure can be from 50 microns to 500 microns, and typically about 100 microns. For example, the first exemplary structure 101 can have the shape of a rectangular pad of 60 microns×100 microns.

An X-ray scan can be performed on the periodic array of unit structures 30 to generate an X-ray scan spectrum. The X-ray scan can be performed by mounting the substrate including the periodic array of unit structures 30 as a target on an X-ray apparatus. If a major crystallographic orientation of the material of the single crystalline semiconductor layer 32 is parallel to the topmost surfaces of the single crystalline semiconductor layer 32, the X-ray diffraction (XRD) geometry illustrated in FIG. 1A may be employed. In general, the angle between the horizontal plane (the plane of the dotted line in FIG. 1A) that is parallel to the topmost surfaces of the single crystalline semiconductor layer 32 and the incident beam need not be the same as the angle between the horizontal plane and the direction of the detector in the X-ray apparatus from the beam spot on the substrate including the periodic array of unit structures 30.

Once an X-ray scan spectrum is generated, a Bragg peak of the material of the single crystalline strained material region 32A can be located in the X-ray scan spectrum. The strain in a direction in the material of the single crystalline strained material region 32A in the periodic array of unit structures 30 can be determined based on the location of the Bragg peak in the X-ray scan spectrum. If the substrate is an SOI substrate including a buried insulator layer 20, the topmost surfaces of the single crystalline semiconductor layer 32 can be parallel to the interface between the buried insulator layer 20 and the single crystalline semiconductor layer 32, which is a top semiconductor layer of the SOI substrate.

The strain in the direction perpendicular to the topmost surface of the single crystalline semiconductor layer 32 can be determined directly from the X-ray scan spectrum based on the Bragg peak shift in the X-ray scan spectrum, i.e., based on the angular shift in the location of the Bragg peak generated from the single crystalline strained material region 32A from an ideal position for a hypothetical Bragg peak that would be present if a material having the composition and crystallographic orientation and not subjected to any external stress were present as a target in the X-ray apparatus. The strain in directions parallel to the topmost surfaces of the single crystalline semiconductor layer 32 can be determined indirectly based on a simulation in which the strain in the direction perpendicular to the topmost surfaces of the single crystalline semiconductor layer 32 as determined through the above method is provided as a boundary condition for performing the simulation. Alternately or additionally, the Poisson's ratio can be provided as a boundary condition in running the simulation to determine the strain in directions parallel to the topmost surfaces of the single crystalline semiconductor layer 32.

The single crystalline strained material region 32A and the single crystalline unstrained material region in each unit structure U can include a first single crystalline semiconductor material, and the at least one stress-generating material region 34 in each unit structure U can include a second single crystalline semiconductor material that is different from the first single crystalline semiconductor material. In each unit structure U, the second single crystalline semiconductor material in the at least one stress-generating material region 34 can be epitaxially aligned to the first single crystalline semiconductor material in the single crystalline strained material region 32A and the single crystalline unstrained material region. The second single crystalline semiconductor material in the at least one stress-generating material region 34 can be embedded in a contiguous portion of the first single crystalline semiconductor material including the single crystalline strained material region and the single crystalline unstrained material region. The contiguous portion can extend throughout the entirety of the single crystalline semiconductor layer 32 with epitaxial alignment throughout.

In one exemplary embodiment, the first single crystalline semiconductor material is single crystalline silicon, and the second single crystalline semiconductor material is a single crystalline alloy of silicon of at least one group IV element other than silicon. The at least one group IV element other than silicon can be carbon and/or germanium.

Referring to FIG. 1C, the first exemplary structure 101 of FIG. 1B is shown in a see-through top-down view in which the at least one dielectric material layer 50 is omitted for clarity. The periodic array of unit structures 30 can have one-dimensional periodicity, i.e., can be repeated in one direction.

Figure 1D:
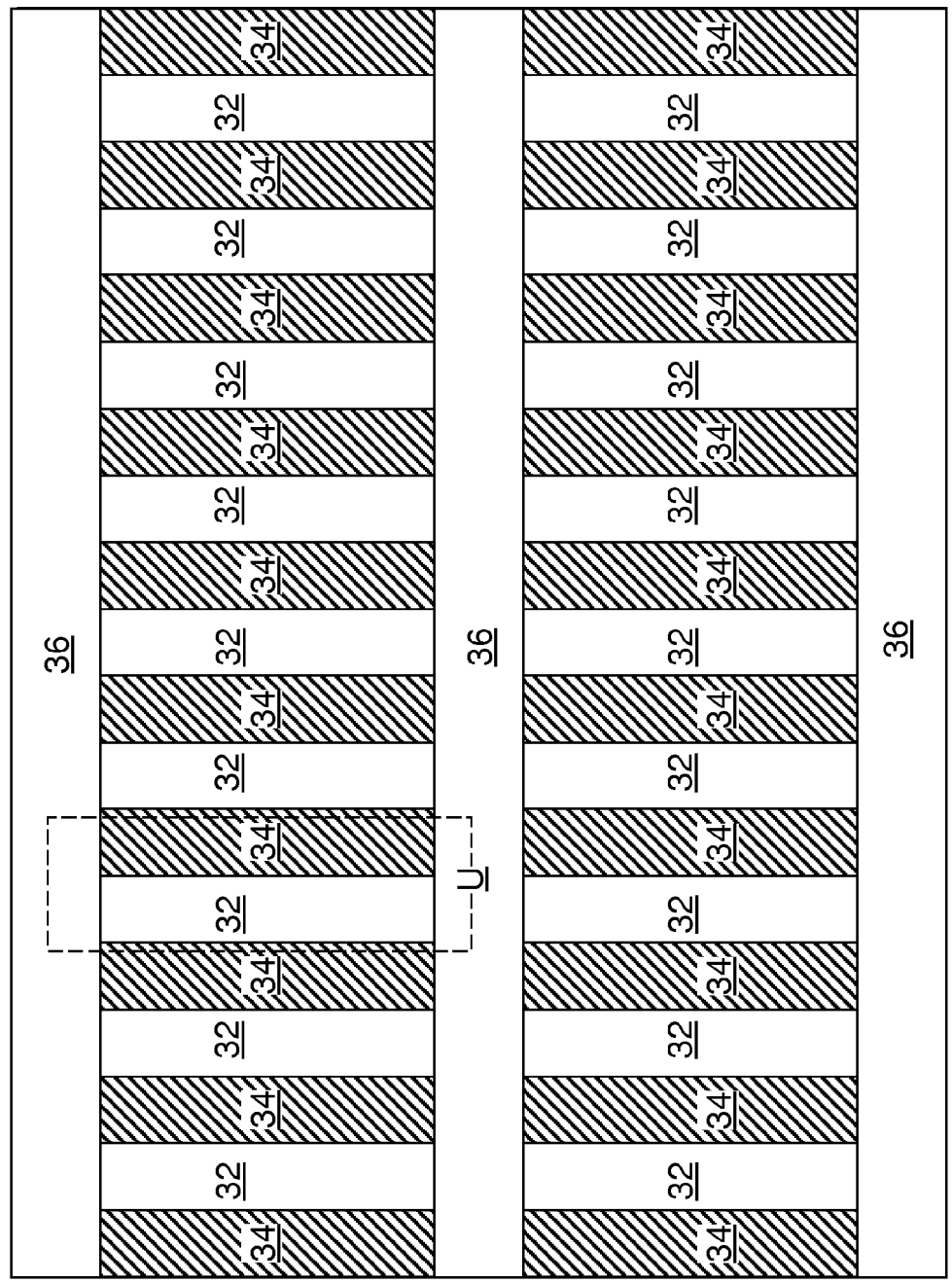
FIG. 1D is a see-through top-down view of a variation of the first exemplary structure according to an embodiment of the present disclosure.

Referring to FIG. 1D, a variation of the first exemplary structure 101 is shown in a see-through top-down view. The variation of the first exemplary structure 101 can have a vertical cross-sectional view that is identical to the vertical cross-sectional view of the first exemplary structure 101 as illustrated in FIG. 1B. The at least one dielectric material layer 50 is omitted for clarity in FIG. 1D. The variation of the first exemplary structure 101 can include shallow trench isolation regions 36 that vertically extends from the topmost surfaces of the single crystalline semiconductor layer 32 to the bottommost surface of the single crystalline semiconductor layer 32, i.e., to the top surface of the buried insulator layer 20. The shallow trench isolation regions 36 simulate shallow trench isolation structures that laterally separate functional semiconductor devices (not shown) that can be formed in a different region of the substrate including the periodic array of unit structures 30. The periodic array of unit structures 30 can have two-dimensional periodicity, i.e., can be repeated in two directions.

Figure 1E:
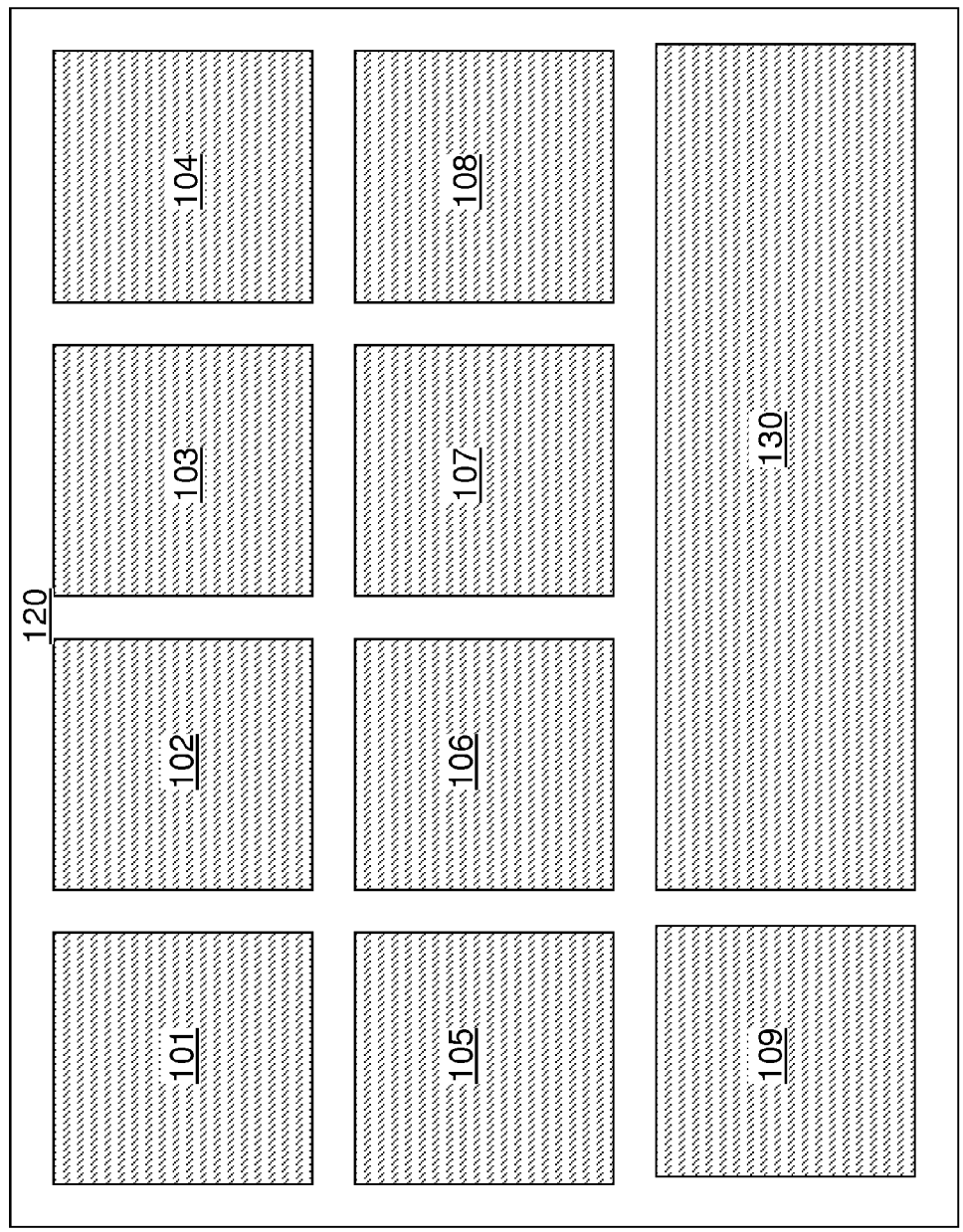
FIG. 1E is a top-down view of a substrate embedding the first exemplary structure according to an embodiment of the present disclosure.

Referring to FIG. 1E, a substrate 120 can be employed to embed the first exemplary structure 101, a second exemplary structure 102, a third exemplary structure 103, a fourth exemplary structure 104, a fifth exemplary structure 105, a sixth exemplary structure 106, a seventh exemplary structure 107, at least another structure 108 configured to provide X-ray diffraction data, a secondary ion mass spectroscopy (SIMS) site structure 109, and at least one semiconductor device region 130. Each of the second exemplary structure 102, the third exemplary structure 103, the fourth exemplary structure 104, the fifth exemplary structure 105, the sixth exemplary structure 106, the seventh exemplary structure 107, and at least another structure 108 includes a periodic array of unit structures located on the substrate 120.

The unit structures in each exemplary structure (101, 102, 103, 104, 105, 106, 107, or 108) can differ from the unit structures in other exemplary structures (101, 102, 103, 104, 105, 106, 107, or 108) by composition or volume of an element corresponding to the single crystalline strained material region 32A or the at least one stress-generating material region 34. For example, the unit structures in the second exemplary structure 102 includes a periodic array of second unit structures on the substrate 120, and the second unit structures can differ from the unit structures in the first exemplary structure 101 by composition or volume of an element corresponding to the single crystalline strained material region 32A or the at least one stress-generating material region 34.

In one embodiment, the various exemplary structures (101, 102, 103, 104, 105, 106, 107, 108) can have the same composition of material for single crystalline unstrained material regions therein. In one embodiment, the at least one stress-generating material region in the various periodic array of unit structures can include the same semiconductor material, and consequently, have the same composition.

Additional X-ray scans can be performed on each periodic array of unit structures located in each of the additional exemplary structures (102, 103, 104, 105, 106, 107, 108) to generate additional X-ray scan spectra. The X-ray scans can be performed by mounting the substrate 120 as a target on an X-ray apparatus. If a major crystallographic orientation of the material of a single crystalline semiconductor layer in each periodic array of unit structures is parallel to the topmost surfaces of the single crystalline semiconductor layer, the X-ray diffraction (XRD) geometry illustrated in FIG. 1A may be employed.

Once the additional X-ray scan spectra are generated, Bragg peaks of the materials of single crystalline strained material regions in each additional exemplary structure (102, 103, 104, 105, 106, 107, 108) can be located in the X-ray scan spectra. The strain in a direction in the material of the single crystalline strained material regions in each periodic array of unit structures can be determined based on the location of the Bragg peaks in the X-ray scan spectra.

The secondary ion mass spectroscopy (SIMS) site structure 109 can be designed to include a planar layer of a material that is the same as the material of the at least one stress-generating material region 34 in the first exemplary structure 101. The SIMS site structure 109 can be employed to analytically determine the composition of the at least one stress-generating material region 34 by destructive or non-destructive analytical means. The at least one semiconductor device region 130 can include functional semiconductor devices having the same configurations, i.e., geometry and composition, as the various periodic arrays of unit structures located in the various exemplary structures (101, 102, 103, 104, 105, 106, 107, 108). The functional semiconductor devices may be configured to pass electrical current therethrough. Passing of the electrical current through the functional semiconductor devices can be effected, for example, by forming contact via structures in the at least one dielectric material layer 50 (See FIG. 1B). In contrast, the various periodic arrays of unit structures located in the various exemplary structures (101, 102, 103, 104, 105, 106, 107, 108) can be configured not to pass any electrical current therethrough, for example, by omitting formation of contact via structures upon the various periodic arrays of unit structures.

The Bragg peak in an X-ray scan spectrum from each single crystalline strained material regions 32A in a periodic array of unit structures 30 in any of the various exemplary structures (101, 102, 103, 104, 105, 106, 107, 108) is shifted from a natural position the same Bragg peak from a hypothetical single crystalline unstrained material region having the same composition and crystallographic orientations as the single crystalline strained material regions 32A. If single crystalline unstrained material regions having the same material composition and crystallographic orientations as the single crystalline strained material regions 32A are present in a periodic array of unit structures 30, the Bragg peak in the X-ray scan spectrum from single crystalline strained material regions 32A in a periodic array of unit structures 30 in any of the various exemplary structures (101, 102, 103, 104, 105, 106, 107, 108) is shifted from the Bragg peak in the X-ray scan spectrum from the single crystalline unstrained material regions, which is at the natural position the Bragg peak as an unstrained material.

Figure 2:
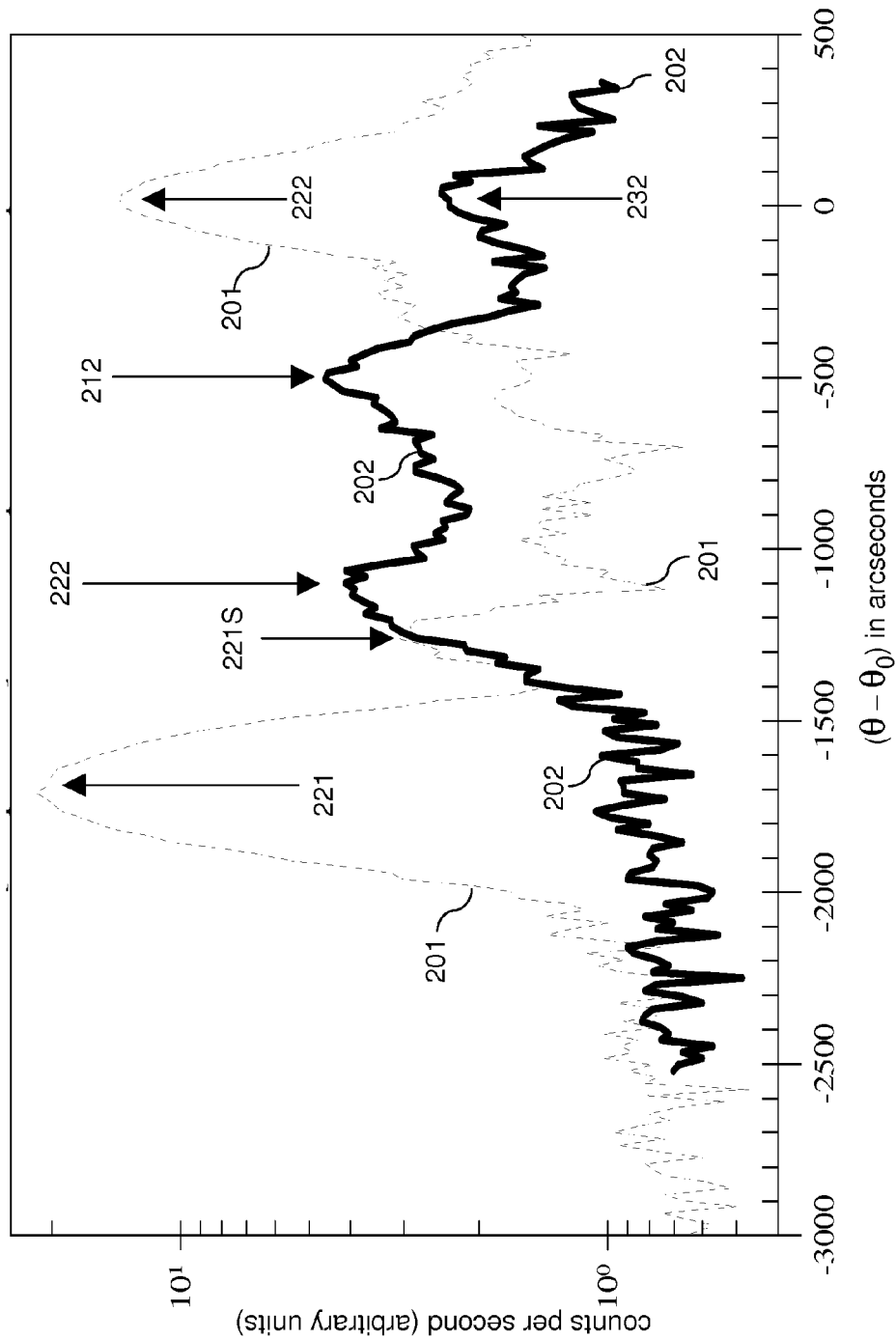
FIG. 2 is a graph including 2θ scan spectra of a sample including a planar lattice mismatched layer and another sample including embedded stress-generating material regions in non-limiting illustrative examples of an embodiment of the present disclosure.

FIG. 2 shows an illustrative example in which a Bragg peak is shifted from a natural position due to strain. Specifically, FIG. 2 is a graph including a first 2θ scan spectrum 201 and a second 2θ scan spectrum 202. The first 2θ scan spectrum 201 is a measured X-ray scan spectrum of a first sample including a planar lattice mismatched layer, and the second 2θ scan spectrum 202 is a measured X-ray scan spectrum of a second sample including embedded stress-generating material regions. The first sample included a vertical stack of a handle substrate containing single crystalline silicon having (100) surface orientation with a miscut, a buried insulator layer including a silicon oxide, a 20 nm thick planar layer of single crystalline silicon having (100) surface orientation, and a 60 nm thick planar layer of single crystalline silicon-germanium alloy having a germanium atomic percentage about 20%, having (100) surface orientation, and epitaxially grown on the 20 nm thick planar layer of single crystalline silicon.

The second sample included a vertical stack of a handle substrate containing single crystalline silicon having (100)

surface orientation with a small miscut, a silicon oxide buried insulator layer, and a periodic array of unit structures formed thereupon. The periodic array of unit structures in the second sample had a structure illustrated in FIGS. 1B and 1C, in which the single crystalline semiconductor layer 32 was a 80 nm thick layer of single crystalline silicon having (100) surface orientation, the at least one stress-generating material region 34 in a unit structure was an embedded single crystalline silicon-germanium alloy region, and a stack 40 of a dielectric material portion 42 and a conductive material portion 44. Each embedded single crystalline silicon-germanium alloy region was epitaxially grown on the layer of single crystalline silicon, had a width about 60 nm and a depth about 60 nm, and had a Ge atomic concentration about 20%. Each stack 40 and each single crystalline strained material region 32A had a width about 45 nm.

The X-ray scans were performed around a (400) Bragg peak of silicon. The angle $2\theta$ corresponding to the (400) Bragg peak is herein referred to as the natural angle $2\theta_0$ for the (400) Bragg peak. The first $2\theta$ scan spectrum 201 shows a prominent peak at $2\theta=2\theta_0$, which coincides with an unstrained silicon (400) Bragg peak 232 from the bottommost 20 nm thick planar layer of single crystalline silicon. Further, the first $2\theta$ scan spectrum 201 shows a SiGe alloy (400) Bragg peak 221 originating from the 60 nm thick planar layer of single crystalline silicon-germanium alloy. In addition, the first $2\theta$ scan spectrum 201 shows a satellite SiGe alloy Bragg peak 221S around the SiGe alloy (400) Bragg peak 221. To locate the unstrained silicon (400) Bragg peak in the first $2\theta$ scan spectrum 201, or to locate the unstrained silicon (400) Bragg peak 232 in the second $2\theta$ scan spectrum 202, alignment of the samples was performed using the Si (400) peak from a silicon handle substrate below the silicon oxide buried insulator layer. Subsequently, the crystallographic orientation of the epitaxial structure above the silicon oxide buried insulator layer was determined using the SiGe peak 221 on the SIMS pad.

The second $2\theta$ scan spectrum 202 shows an unstrained silicon (400) Bragg peak 232 at $2\theta=2\theta_0$ from the unstrained portion of the 80 nm thick layer of single crystalline silicon in the second sample. The second $2\theta$ scan spectrum 202 also includes a strained silicon (400) Bragg peak 212 from the strained portion of the 80 nm thick layer of single crystalline silicon in the second sample, i.e., the portion of the 80 nm thick layer of single crystalline silicon located above the bottommost surfaces of the embedded single crystalline silicon-germanium alloy regions, between a neighboring pair of embedded single crystalline silicon-germanium alloy regions, and directly underneath stack 40 (See FIG. 1B) of a dielectric material portion 42 and a conductive material portion 44. Each strained portion of the 80 nm thick layer of single crystalline silicon in the second sample corresponds to a single crystalline strained material region 32A in FIG. 1B.

Further, the second $2\theta$ scan spectrum 201 shows a SiGe alloy (400) Bragg peak 222 originating from the embedded single crystalline silicon-germanium alloy regions. Because the volume of the embedded single crystalline silicon-germanium alloy regions in the second sample is less than the volume of the silicon germanium alloy in the 60 nm thick planar layer of single crystalline silicon-germanium alloy, the integrated area of the SiGe alloy (400) Bragg peak 222 is less than the integrated area of the SiGe alloy (400) Bragg peak 221 in the first $2\theta$ scan spectrum 201.

The fact that the location of the strained silicon (400) Bragg peak 212 in the second $2\theta$ scan spectrum 202 can be determined relative to the unstrained silicon (400) Bragg peak 232 illustrates that direct measurement of strain in single crystalline strained material regions 32A is possible. The direction of the measured strain corresponding to the Bragg peak shift, i.e., the difference in $2\theta$ angles between the strained silicon (400) Bragg peak 212 and the unstrained silicon (400) Bragg peak 232, is the direction perpendicular to the atomic planes that generate the X-ray scan spectrum. If the atomic planes that generate the X-ray scan spectrum are parallel to the topmost surface of a single crystalline semiconductor material layer in a substrate, the measured strain is the strain in the direction perpendicular to the topmost surface of a single crystalline semiconductor material layer.

In general, it is not necessary for the atomic planes that generate the X-ray scan spectrum to be parallel to the topmost surface of a single crystalline semiconductor material layer in a substrate or an interface between a single crystalline semiconductor material layer and a buried insulator layer. Thus, by mounting a substrate in a manner that enables selection of the atomic planes that generate the X-ray scan spectrum from among arbitrary set of parallel planes, direct measurement the strain in any direction in single crystalline strained material regions is possible. To effect such direct strain measurement in arbitrary directions, a target mounting system equipped with three-dimensional target rotation capability can be employed. Alternatively an asymmetric scan condition such as the (224) Bragg peak can be used to directly measure the strain in directions both parallel and perpendicular to the atomic planes. If an asymmetric Bragg peak is selected a full reciprocal space map should be recorded as the strained Si and SiGe Bragg peaks will shift.

The X-rays scan of the present disclosure is a non-destructive measurement method. As such, X-ray scans can be performed between any processing steps in a sequence of processing steps employed to manufacture semiconductor devices in semiconductor fabrication facilities.

Figure 3A:
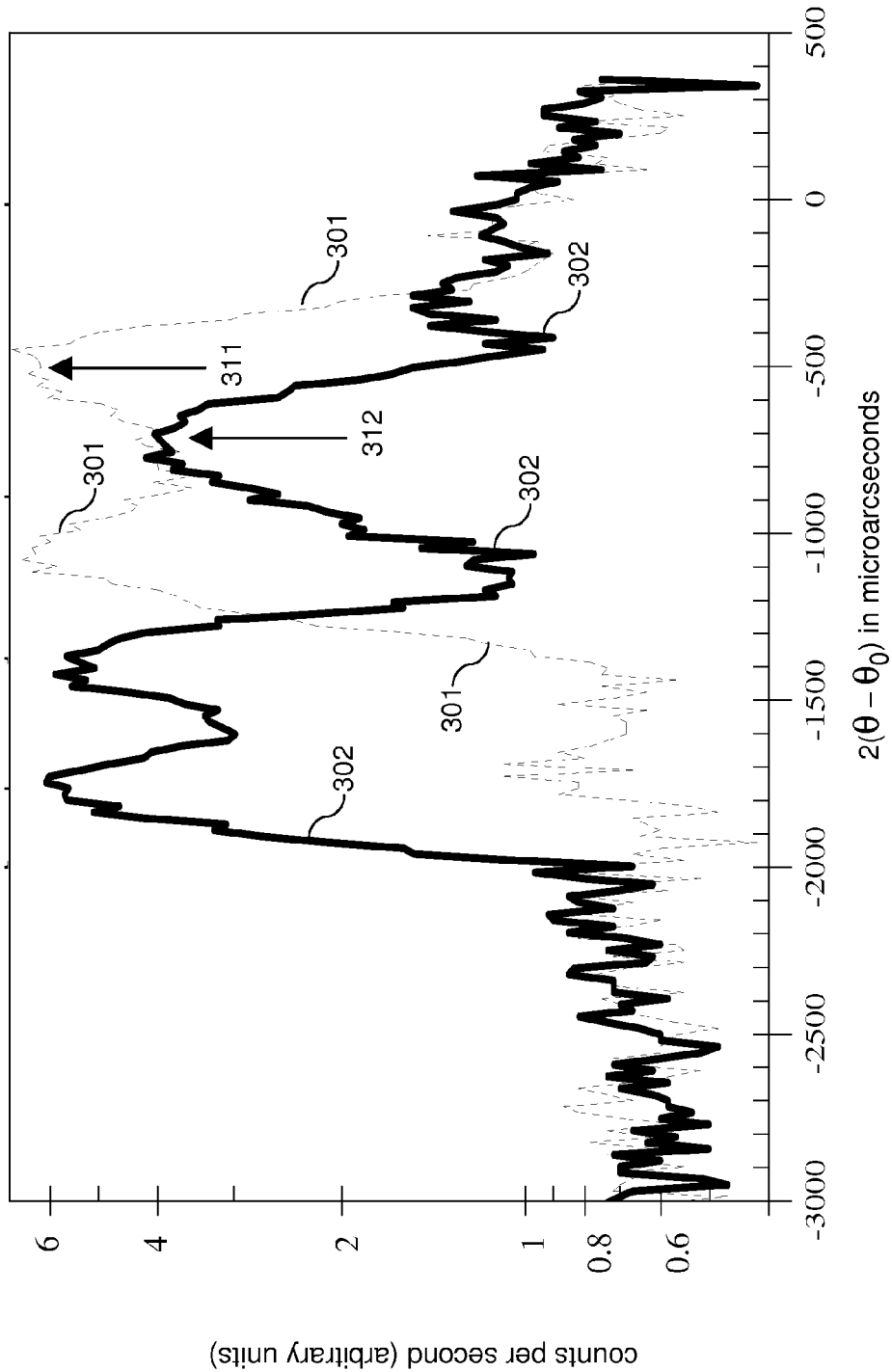
FIG. 3A is a graph including 2θ scan spectra of samples including different percentages of germanium in embedded SiGe alloy regions after deposition of the material in the embedded SiGe alloy regions according to non-limiting illustrative examples of an embodiment of the present disclosure.

For example, FIG. 3A illustrates a third $2\theta$ scan spectrum 301 of a third sample and a fourth $2\theta$ scan spectrum 302 of a fourth sample. The third $2\theta$ scan spectrum 301 and the fourth $2\theta$ scan spectrum 302 were generated from the third and fourth sample, respectively, immediately after deposition of embedded single crystalline silicon-germanium alloy regions and before performing any additional processing steps.

The third sample and the fourth sample differed only by the atomic concentration of germanium in embedded single crystalline silicon-germanium alloy regions. The third sample and the fourth sample had a periodic array of unit structures. Each periodic array of unit structures had an 80 nm thick layer of single crystalline silicon having (100) surface orientation, embedded single crystalline silicon-germanium alloy regions, and a stack 40 of a dielectric material portion 42 and a conductive material portion 44. Each embedded single crystalline silicon-germanium alloy regions was epitaxially aligned to the layer of single crystalline silicon, had a width about 60 nm and a depth about 60 nm. Each stack 40 and each single crystalline strained material region 32A had a width about 45 nm. The embedded single crystalline silicon-germanium alloy regions in the third sample had a Ge atomic concentration about 20%. The embedded single crystalline silicon-germanium alloy regions in the third sample had a Ge atomic concentration about 27%.

The third $2\theta$ scan spectrum 301 includes a strained silicon (400) Bragg peak 311, and the third $2\theta$ scan spectrum 301 includes a strained silicon (400) Bragg peak 312. The magnitude of the Bragg peak shift in the strained silicon (400) Bragg peak relative to a natural (i.e., unstrained) silicon (400) Bragg peak (corresponding to $2\theta=2\theta_0$) increases with the Ge atomic concentration in the embedded single crystalline silicon-germanium alloy regions.

The third sample and the fourth sample were subjected to additional processing after the XRD measurement that generated the third 2θ scan spectrum 301 and the fourth 2θ scan spectrum 302. Specifically, dielectric gate spacer deposition processes, halo and extension ion implantation processes, and a rapid thermal anneal (RTA) process were sequentially performed. Additional XRD measurements were performed after the RTA process.

Figure 3B:
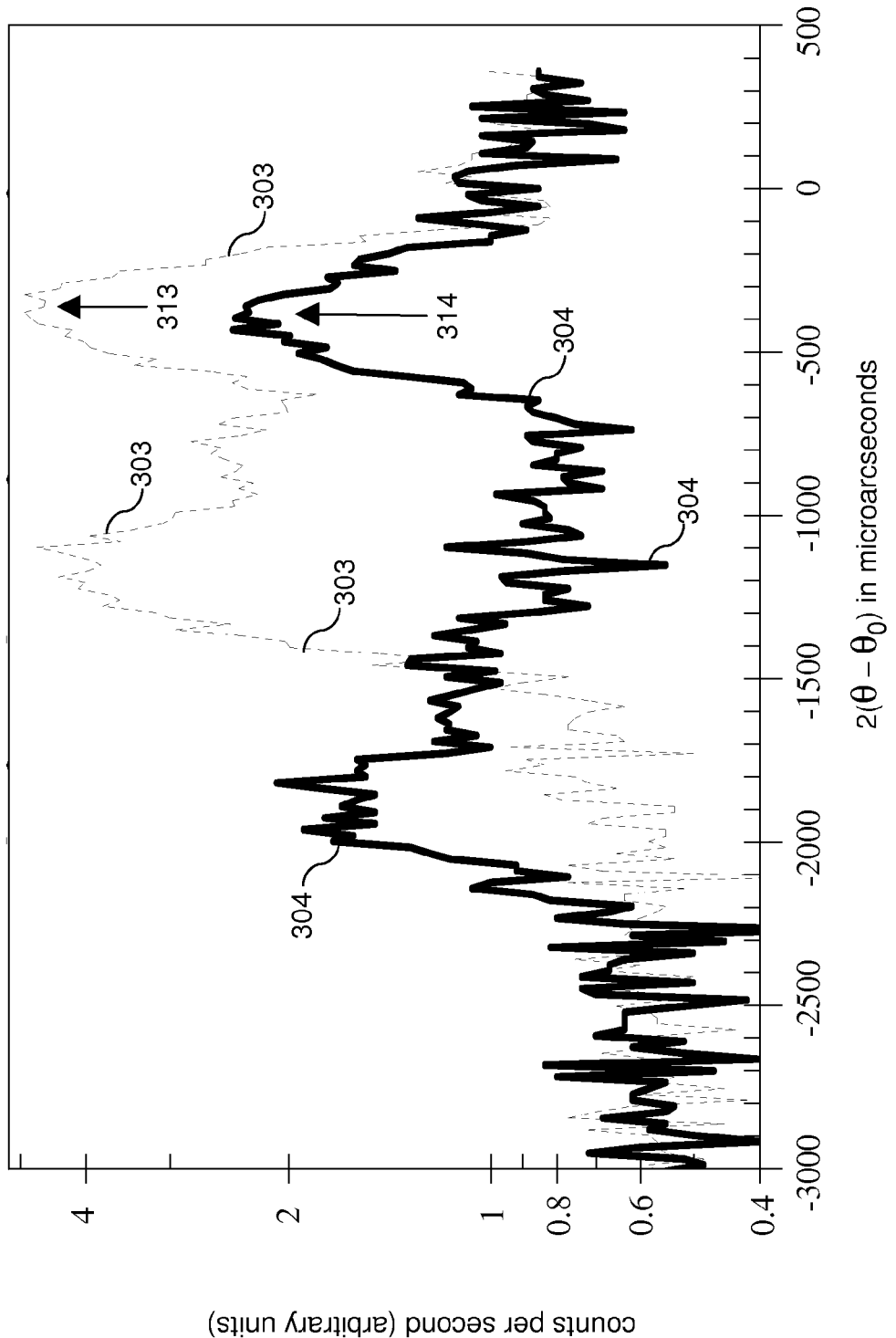
FIG. 3B is a graph including 2θ scan spectra of samples including different percentages of germanium in embedded SiGe alloy regions after rapid thermal anneal (RTA) of the material in the embedded SiGe alloy regions according to non-limiting illustrative examples of an embodiment of the present disclosure.

Referring to FIG. 3B, a fifth 2θ scan spectrum 303 of the third sample and a sixth 2θ scan spectrum 304 of the fourth sample are shown. The fifth 2θ scan spectrum 303 and the sixth 2θ scan spectrum 304 were generated from the third and fourth sample, respectively, after performing additional post-epitaxial growth processing steps.

The fifth 2θ scan spectrum 303 includes a strained silicon (400) Bragg peak 313, which is shifted from the corresponding strained silicon (400) Bragg peak 311 in the third 2θ scan spectrum 301. Likewise, the sixth 2θ scan spectrum 304 includes a strained silicon (400) Bragg peak 314, which is shifted from the corresponding strained silicon (400) Bragg peak 312 in the fourth 2θ scan spectrum 302. As illustrated by the third, fourth, fifth, and sixth fifth 2θ scan spectra (301, 302, 303, 304), the strained silicon Bragg peak shift can be monitored in-situ between any processing steps of the sequence of processing steps employed to manufacture semiconductor devices in semiconductor fabrication facilities.

Figure 4:
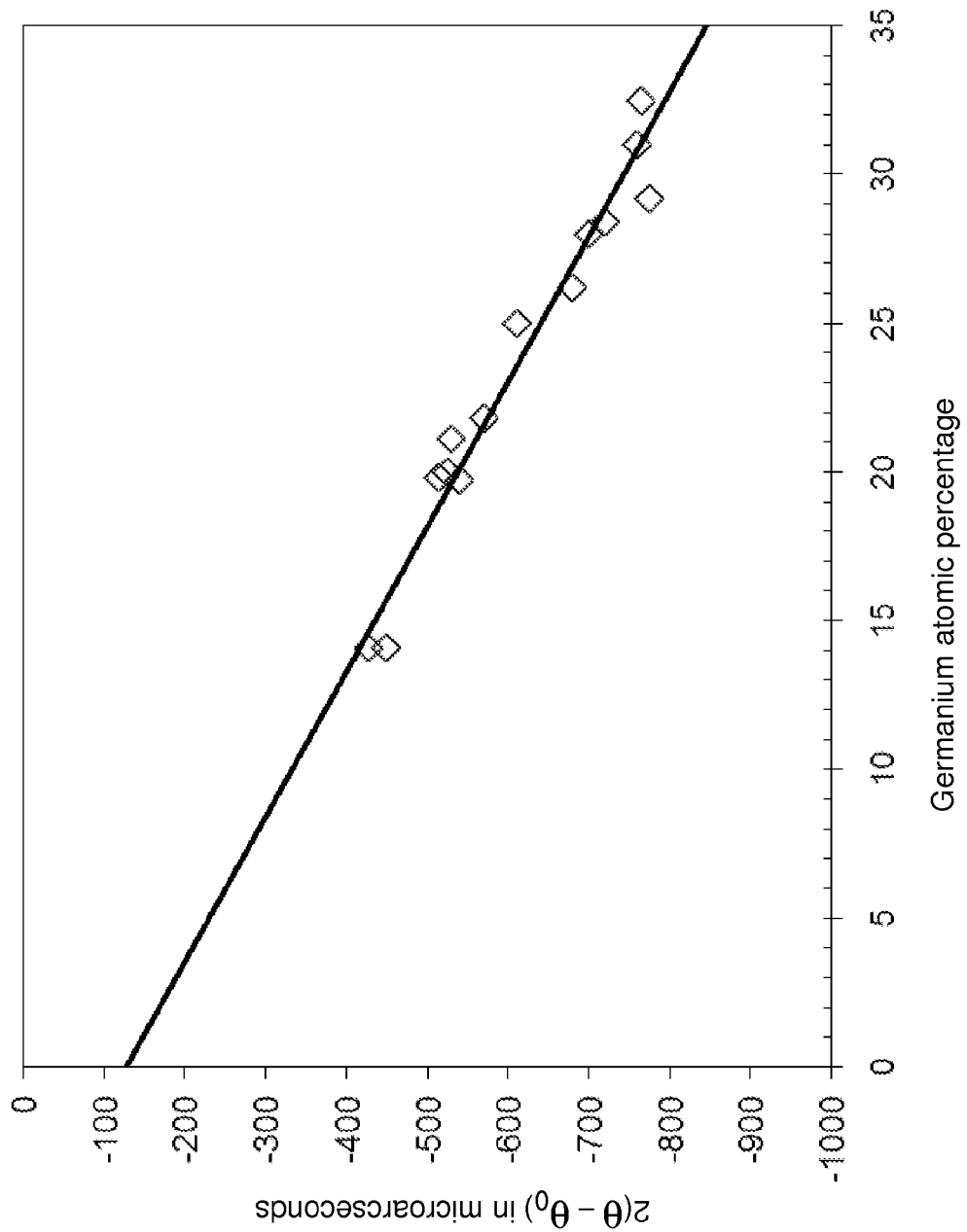
FIG. 4 is a graph illustrating a correlation between the atomic percentages of germanium in embedded SiGe alloy regions and a Bragg peak shift after deposition according to a non-limiting illustrative example of an embodiment of the present disclosure.

In case the stress-generating material regions 34 (See FIGS. 1B-1D) include a semiconductor alloy having a different lattice constant than the semiconductor material of the single crystalline semiconductor layer 32 (See FIGS. 1B-1D), the atomic composition of the stress-generating material regions 34 can be monitored immediately after deposition of the material of the stress-generating material regions 34 or at any processing step thereafter. For example, FIG. 4 illustrates a correlation between the atomic percentages of germanium in embedded SiGe alloy regions immediately after deposition of the material of the stress-generating material regions 34 and a Bragg peak shift. In this case, the stress-generating material regions 34 included single crystalline silicon germanium alloy portions epitaxially aligned to a single crystalline silicon layer that functions as the single crystalline semiconductor layer 32. This correlation was established based on XRD data generated immediately after deposition. By establishing a correlation between the measured Bragg peak shift and atomic percentage of an element at any processing step after deposition (including the step immediately after deposition), the composition of the stress-generating material regions 34 can be monitored in a non-destructive manner, and the information can be employed to monitor the deposition process for the stress-generating material regions 34.

Figure 5:
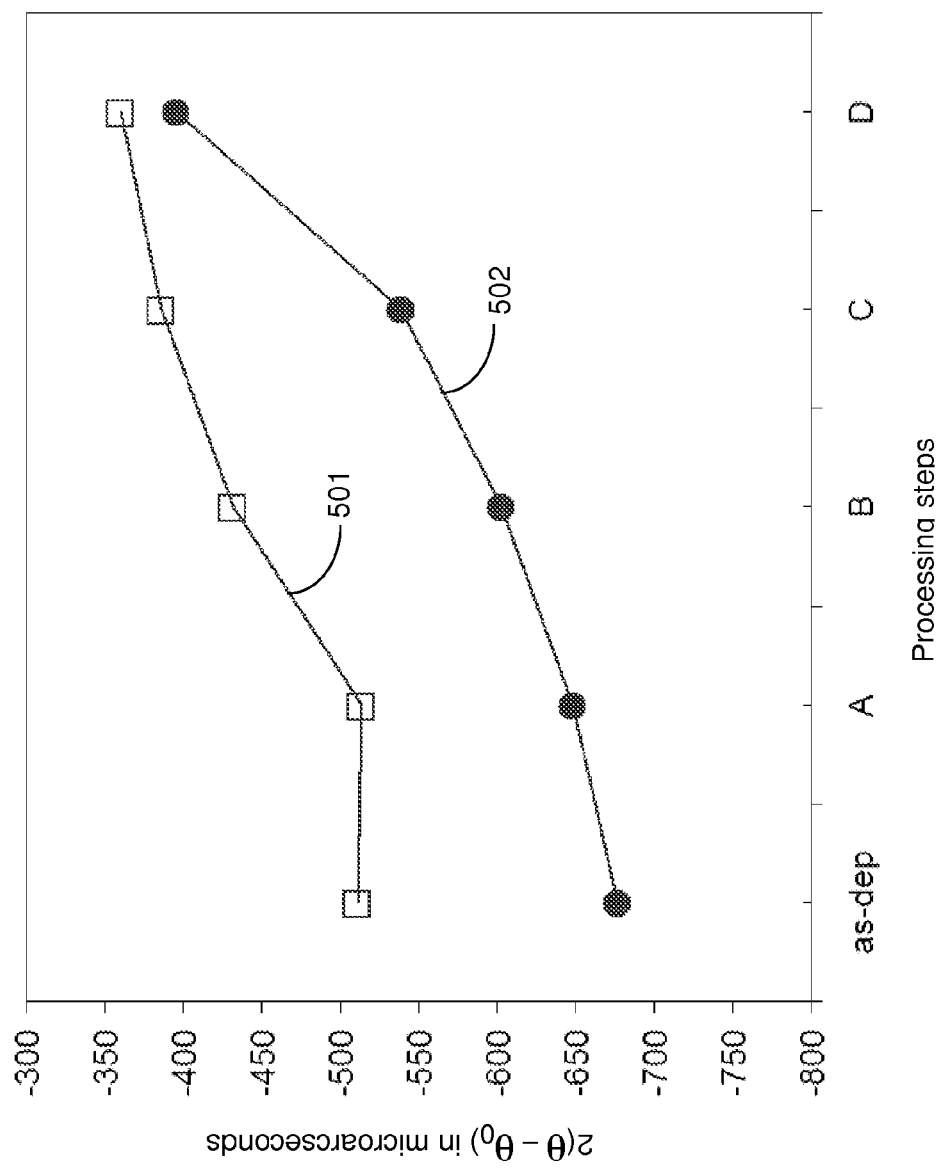
FIG. 5 is a graph illustrating changes in a Bragg peak shift in two samples at various stages of a processing sequence according to a non-limiting illustrative example of an embodiment of the present disclosure.

Because the XRD measurement of the present disclosure is a non-destructive measurement, the change in strain in single crystalline strained material regions 32A (See FIG. 1B) can be monitored at any time after deposition of the stress-generating material regions 34 and throughout the sequence of processing steps employed to manufacture semiconductor devices in semiconductor fabrication facilities. Referring to FIG. 5, the Bragg peak shift in the third sample as a function of processing steps is plotted in a first curve 501, and the Bragg peak shift in the fourth sample as a function of processing steps is plotted in a second curve 502 to illustrate an aspect of the present disclosure that enables continuous monitoring of strain throughout a sequence of processing steps during manufacturing of semiconductor devices.

Referring to FIG. 6A, a second exemplary structure 102 is illustrated. The second exemplary structure 102 can be derived from the first exemplary structure 101 (See FIGS. 1B, 1C, and 1E) or a variation thereof (See FIG. 1D) by changing the lateral dimension (i.e., the width) of the stress-generating material regions 34. In one exemplary case, the width of the stress-generating material regions 34 in the second exemplary structure 102 can be twice the width of the stress-generating material regions 34 in the first exemplary structure 101. The width of the single crystalline strained material regions 32A in the second exemplary structure 102 may be the same as the width of the single crystalline strained material regions 32A in the first exemplary structure 101, or can be altered as needed.

Referring to FIG. 6B, a third exemplary structure 103 is illustrated. The third exemplary structure 103 can be derived from the first exemplary structure 101 (See FIGS. 1B, 1C, and 1E) or a variation thereof (See FIG. 1D) by changing the lateral dimension (i.e., the width) of the stress-generating material regions 34. In one exemplary case, the width of the stress-generating material regions 34 in the third exemplary structure 103 can be four times the width of the stress-generating material regions 34 in the first exemplary structure 101. The width of the single crystalline strained material regions 32A in the third exemplary structure 103 may be the same as the width of the single crystalline strained material regions 32A in the first exemplary structure 101, or can be altered as needed.

Figure 7:
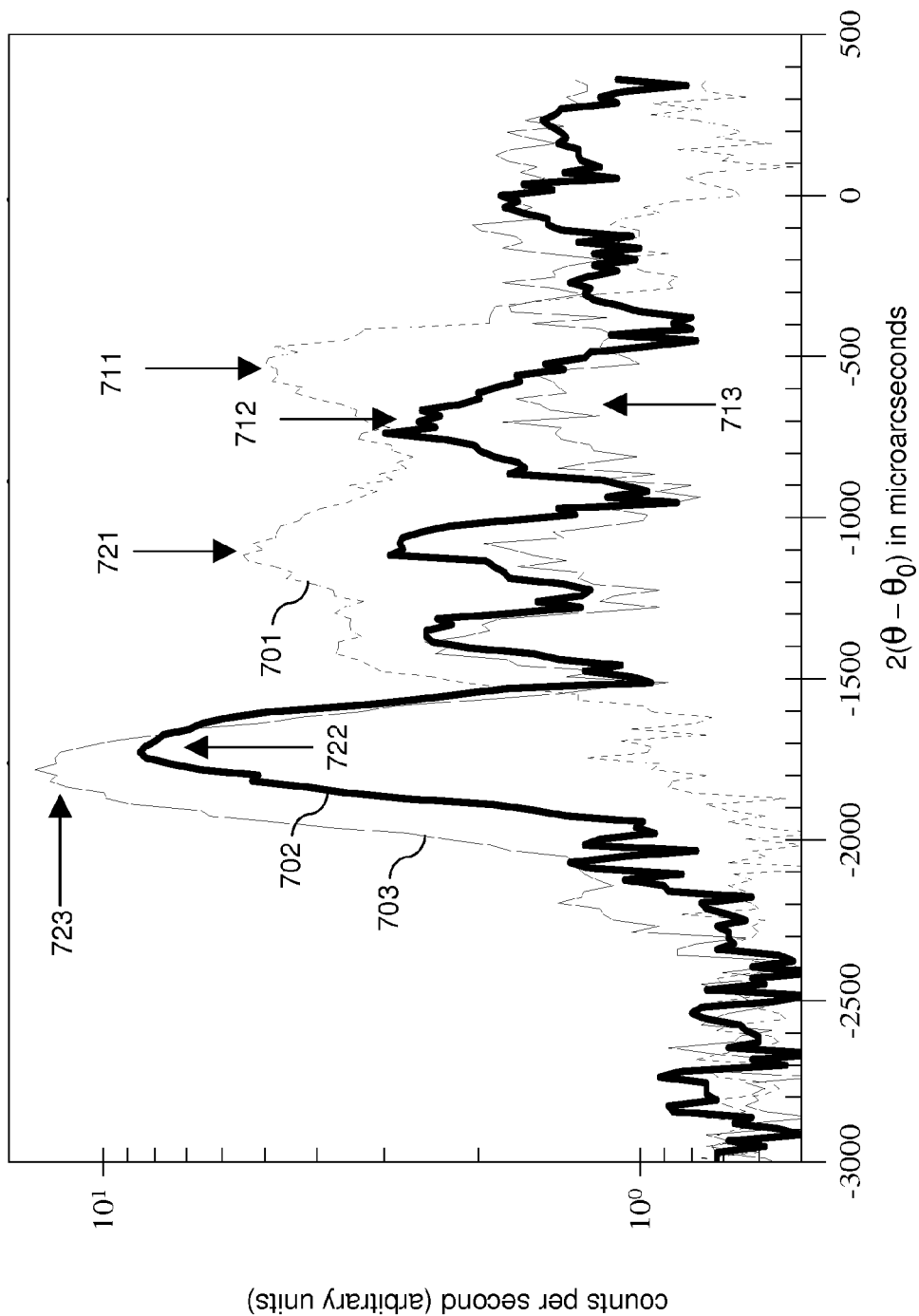
FIG. 7 is a graph including 2θ scan spectra of a reference sample including the planar layer of the lattice mismatched layer and a sample including the first exemplary structure of FIG. 1B, the second exemplary structure of FIG. 6A, and the third exemplary structure of FIG. 6B in non-limiting illustrative examples of an embodiment of the present disclosure.

Referring to FIG. 7, the graphs shows a seventh 2θ scan spectrum 701 of the first exemplary structure 101 of FIG. 1B, a eighth 2θ scan spectrum 702 of the second exemplary structure 102 of FIG. 6A, and a ninth 2θ scan spectrum 703 of the third exemplary structure 103 of FIG. 6B. Each periodic array of unit structures had an 80 nm thick layer of single crystalline silicon having (100) surface orientation, embedded single crystalline silicon-germanium alloy regions, and a stack 40 of a dielectric material portion 42 and a conductive material portion 44. Each embedded single crystalline silicon-germanium alloy region was epitaxially grown on the layer of single crystalline silicon, and differed only in the relative width of the embedded single crystalline silicon-germanium alloy region. The embedded single crystalline silicon-germanium alloy regions in the fifth sample had a Ge atomic concentration about 20%.

The fifth sample had the same structure and composition as the first sample except that the stress-generating material regions 34 were modified to have a width about 120 nm in the fifth sample. The sixth sample had the same structure and composition as the first sample except that the stress-generating material regions 34 were modified to have a width about 240 nm in the sixth sample.

The seventh 2θ scan spectrum 701 shows a strained silicon (400) Bragg peak 711 from the strained portion of the 80 nm thick layer of single crystalline silicon in the second sample, i.e., the portion of the 80 nm thick layer of single crystalline silicon located above the bottommost surfaces of the embedded single crystalline silicon-germanium alloy regions, between a neighboring pair of embedded single crystalline silicon-germanium alloy regions, and directly underneath stack 40 (See FIG. 1B) of a dielectric material portion 42 and a conductive material portion 44. Each strained portion of the 80 nm thick layer of single crystalline silicon in the second sample corresponds to a single crystalline strained material region 32A in FIG. 1B. Further, the seventh 2θ scan spectrum 701 shows a SiGe alloy (400) Bragg peak 721 originating from the embedded single crystalline silicon-germanium alloy regions.

The eighth 2θ scan spectrum 702 shows a strained silicon (400) Bragg peak 712 from the strained portion of the 80 nm thick layer of single crystalline silicon in the fifth sample, i.e., the portion of the 80 nm thick layer of single crystalline silicon located above the bottommost surfaces of the embedded single crystalline silicon-germanium alloy regions, between a neighboring pair of embedded single crystalline silicon-germanium alloy regions, and directly underneath stack 40 (See FIG. 6A) of a dielectric material portion 42 and a conductive material portion 44. Each strained portion of the 80 nm thick layer of single crystalline silicon in the fifth sample corresponds to a single crystalline strained material region 32A in FIG. 6A. Further, the eighth 2θ scan spectrum 702 shows a SiGe alloy (400) Bragg peak 722 originating from the embedded single crystalline silicon-germanium alloy regions.

Because the relative size of the embedded single crystalline silicon-germanium alloy regions relative to the size of the strained portion of the 80 nm thick layer of single crystalline silicon is greater in the fifth sample than in the second sample, the strained portion of the 80 nm thick layer is strained more in the fifth sample than in the second sample. Thus, the Bragg peak shift of the SiGe alloy (400) Bragg peak 722 is greater than the Bragg peak shift of the SiGe alloy (400) Bragg peak 721. Because less amount of material is present for the strained portion of the 80 nm thick layer of single crystalline silicon in the fifth sample than in the second sample, the integrated area of the strained silicon (400) Bragg peak 712 is less than the integrated area of the strained silicon (400) Bragg peak 711. Because more amount of material is present for the embedded single crystalline silicon-germanium alloy regions in the fifth sample than in the second sample, the integrated area of the SiGe alloy (400) Bragg peak 722 is greater than the integrated area of the SiGe alloy (400) Bragg peak 721.

The ninth 2θ scan spectrum 703 shows a strained silicon (400) Bragg peak 713 from the strained portion of the 80 nm thick layer of single crystalline silicon in the sixth sample, i.e., the portion of the 80 nm thick layer of single crystalline silicon located above the bottommost surfaces of the embedded single crystalline silicon-germanium alloy regions, between a neighboring pair of embedded single crystalline silicon-germanium alloy regions, and directly underneath stack 40 (See FIG. 6B) of a dielectric material portion 42 and a conductive material portion 44. Each strained portion of the 80 nm thick layer of single crystalline silicon in the sixth sample corresponds to a single crystalline strained material region 32A in FIG. 6B. Further, the ninth 2θ scan spectrum 703 shows a SiGe alloy (400) Bragg peak 723 originating from the embedded single crystalline silicon-germanium alloy regions.

Because the relative size of the embedded single crystalline silicon-germanium alloy regions relative to the size of the strained portion of the 80 nm thick layer of single crystalline silicon is greater in the sixth sample than in the fifth sample, the strained portion of the 80 nm thick layer is strained more in the sixth sample than in the fifth sample. Thus, the Bragg peak shift of the SiGe alloy (400) Bragg peak 723 is greater than the Bragg peak shift of the SiGe alloy (400) Bragg peak 722. Because less amount of material is present for the strained portion of the 80 nm thick layer of single crystalline silicon in the sixth sample than in the fifth sample, the integrated area of the strained silicon (400) Bragg peak 713 is less than the integrated area of the strained silicon (400) Bragg peak 712. Because more amount of material is present for the embedded single crystalline silicon-germanium alloy regions in the sixth sample than in the fifth sample, the integrated area of the SiGe alloy (400) Bragg peak 723 is greater than the integrated area of the SiGe alloy (400) Bragg peak 722.

In general, the effect of variations in geometry on the strain of any single crystalline strained material region can be monitored and quantified by comparing measured strain from various structures having different periodic arrays of unit structures designed to simulate the variations in geometry.

Figure 8:
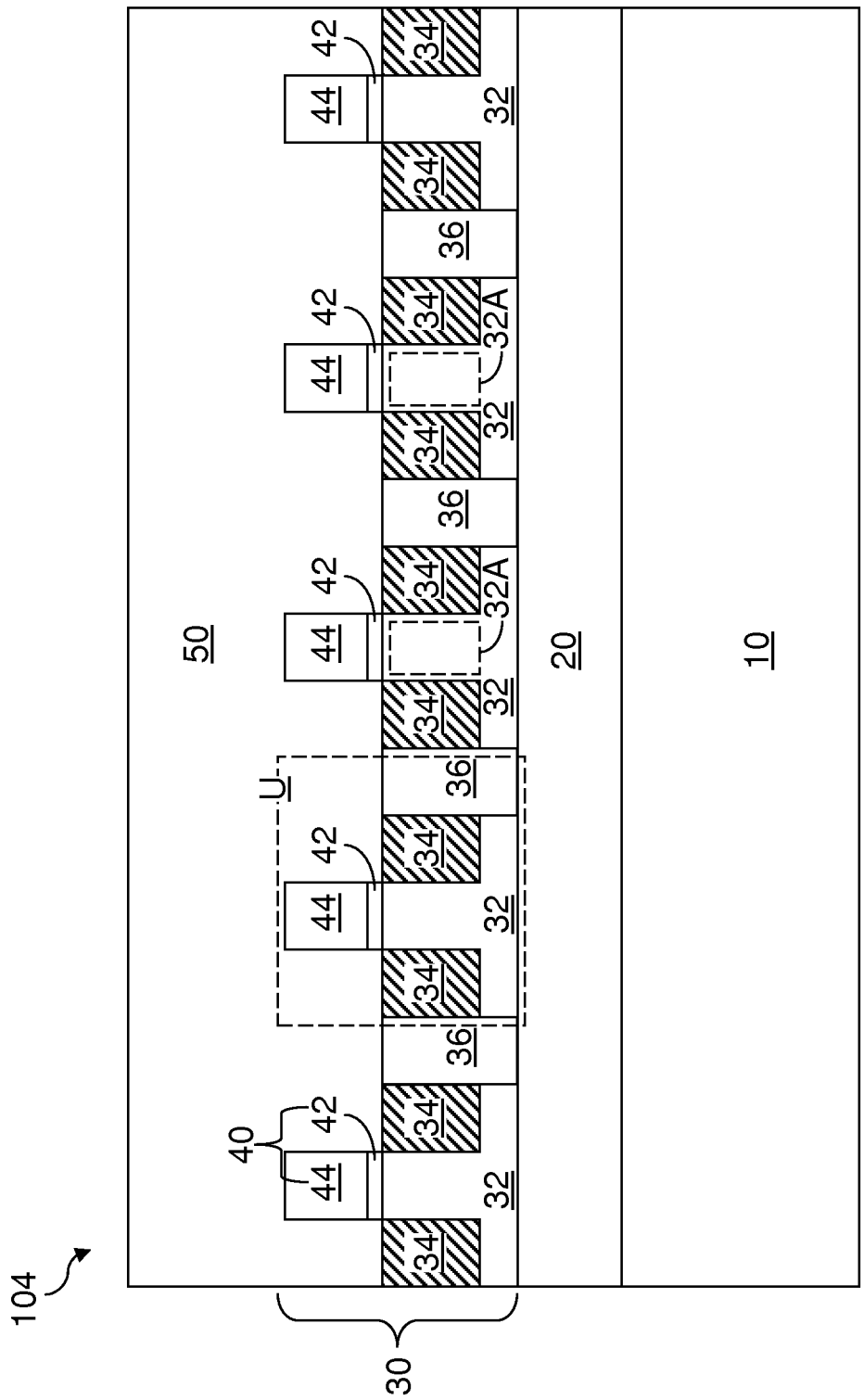
FIG. 8 is a vertical cross-sectional view of a fourth exemplary structure according to an embodiment of the present disclosure.

Referring to FIG. 8, a fourth exemplary structure 104 can be derived from the variation of the first exemplary structure 101 as illustrated in FIG. 1D, or any similar variation of the second or third exemplary structures (102, 103) by extending the area of the shallow trench isolation regions 36 to replace every other single crystalline strained material region 32A with an extended portion of the shallow trench isolation regions 36. The stacks 40 of a dielectric material portion 42 and a conductive material portion 44 are removed from above the shallow trench isolation regions 36 as extended.

Figure 9:
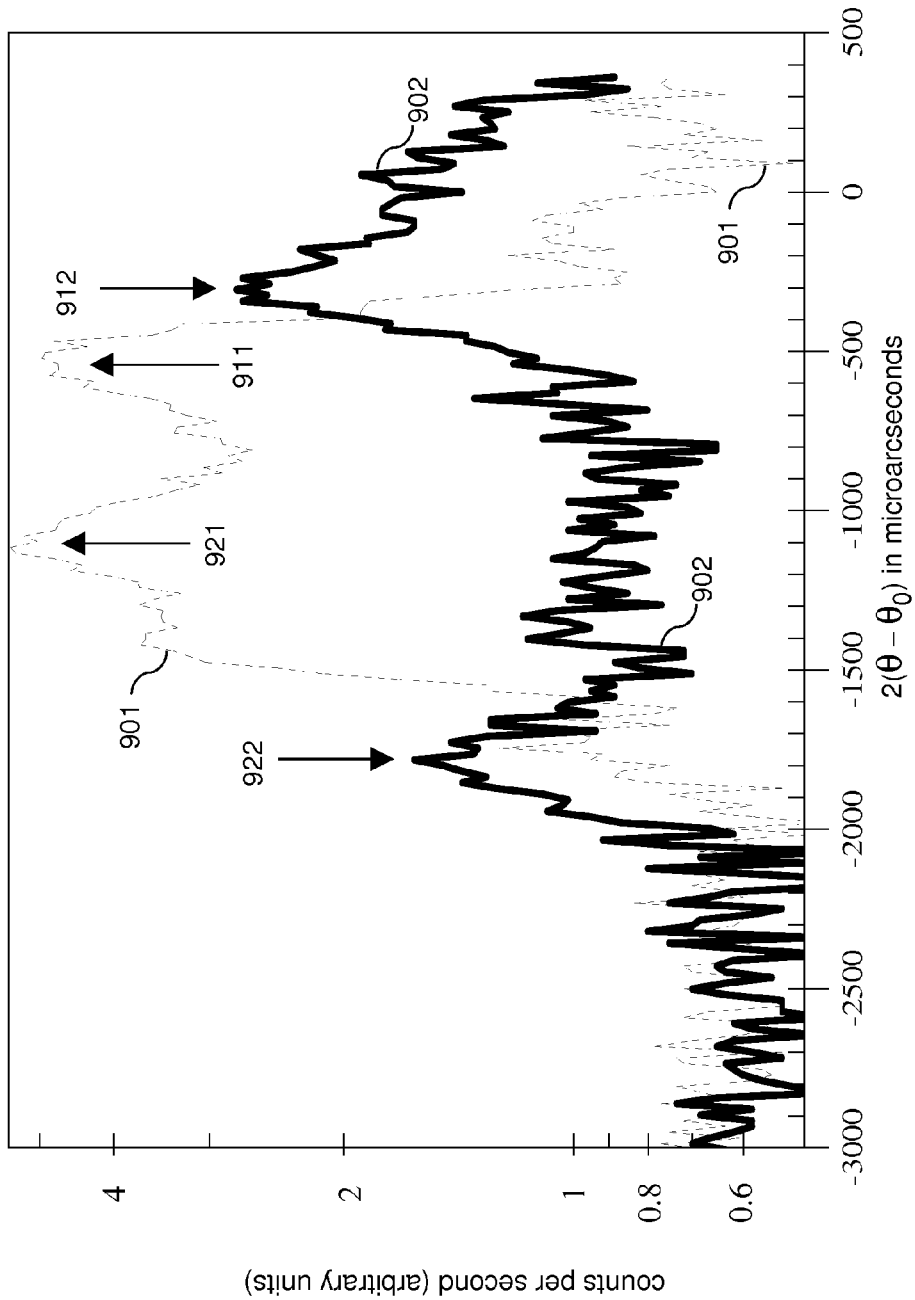
FIG. 9 is a graph including 2θ scan spectra of a sample including the first exemplary structure of FIG. 1B and a sample including the fourth exemplary structure of FIG. 8 in non-limiting illustrative examples of an embodiment of the present disclosure.

Referring to FIG. 9, a tenth 2θ scan spectrum 901 of a sample including a variation of the first exemplary structure of FIG. 1B and an eleventh 2θ scan spectrum 902 of a sample including the fourth exemplary structure 104 of FIG. 8 are shown. In this example, the samples differed only by the presence or absence of the extended portions of the shallow trench isolation regions 36 between every other adjacent pair of stress-generating material regions 34. Comparison of the tenth 2θ scan spectrum 901 and the eleventh 2θ scan spectrum 902 shows that the magnitude of the Bragg peak shift is reduced if extended portions of the shallow trench isolation regions 36 are present.

Referring to FIG. 10, a fifth exemplary structure 105 can be derived from any of the first, second, or third exemplary structures (101, 102, 103) by removing the stacks 40 of a dielectric material portion 42 and a conductive material portion 44. The fifth exemplary structure 105 illustrates that the periodic array of unit structures does not need to include stacks 40 of a dielectric material portion 42 and a conductive material portion 44 in some embodiments.

Referring to FIG. 11, a sixth exemplary structure 106 can be derived from the fourth exemplary structure 104 by removing the stacks 40 of a dielectric material portion 42 and a conductive material portion 44. Like the fifth exemplary structure 105, the sixth exemplary structure 106 illustrates that the periodic array of unit structures does not need to include stacks 40 of a dielectric material portion 42 and a conductive material portion 44 in some embodiments.

Figure 12:
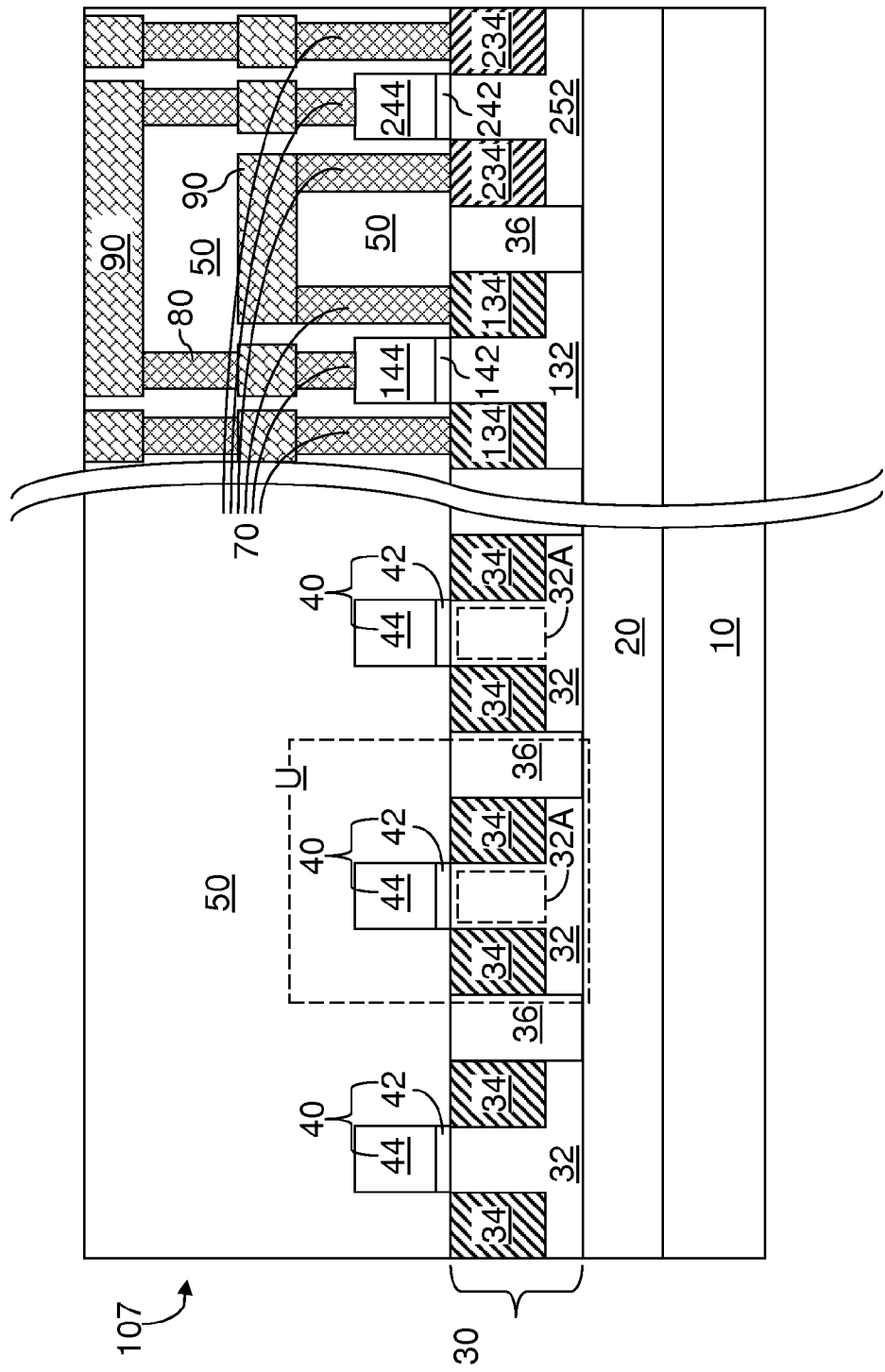
FIG. 12 is a vertical cross-sectional view of a seventh exemplary structure according to an embodiment of the present disclosure.

Referring to FIG. 12, a seventh exemplary structure 107 can be derived from any combination of the first through sixth exemplary structures (101-106) and any semiconductor structures that can be formed concurrently with formation of any of the first through sixth exemplary structures (101-106).

The periodic array of unit structures U does not need to be provided with any electrical contacts because the periodic array of unit structures U does not need to include any functional semiconductor device. In one embodiment, each of the unit structures U may includes a stack structure, i.e., a stack 40 that includes a dielectric material portion 42 and a conductive material portion 44. The stack structure can contact and overlie a single crystalline strained material region 32A, and the conductive material portion 44 can be encapsulated by the dielectric material portion 42 and at least one dielectric material layer 50 without contacting any conductive structure such as contact via structures.

A field effect transistor can be provided in an area of the substrate that is different from the area of including a periodic array of unit structures. The field effect transistor can include a gate dielectric (142 or 242) having a same material composition and thickness as the dielectric material portion 42. Further, the field effect transistor can include a gate electrode (144 or 244) having a same material composition and thickness as the conductive material portion 44. The field effect transistor may include another single crystalline semiconductor layer (132 or 252) that has the same thickness and composition as the single crystalline semiconductor layer 32. Alternately, the dopant type and/or the dopant concentration in the other single crystalline semiconductor layer (132 or 252) may be different from the single crystalline semiconductor layer 32, while the other single crystalline semiconductor layer (132 or 252) and the single crystalline semiconductor layer 32 may have the same composition excluding the dopant components.

One type of field effect transistors may include embedded source and drain regions 134 which have the same material composition and dimensions as a stress-generating material region 34. Another type of field effect transistors may include additional embedded source and drain regions 234 which have a different material composition than a stress-generating material regions 34. In this case, additional periodic array(s) of unit structures including different stress-generating material regions that have the same material composition as the additional embedded source and drain regions 234 may be employed to monitor the effect of the additional embedded source and drain regions 234 on a channel of a transistor. For example, one set of periodic arrays of unit structures may be configured to monitor the effect of embedded silicon-germanium alloy regions on the strain in a channel of one type of transistors, while another set of periodic arrays of unit structures may be configured to monitor the effect of embedded silicon-carbon alloy regions on the strain in a channel of another type of transistors.

Any functional semiconductor device formed on the substrate can be configured to flow electrical current through a single crystalline strained material region therein such as the channel of a field effect transistor including embedded source and drain regions (134, 234) including a material different from the material of the other single crystalline semiconductor layer (132 or 252). The at least one periodic array of unit structures can be employed to monitor the strain in the functional semiconductor devices. In this case, the other single crystalline strained material region (134, 234) can have a same material as the single crystalline strained material region 32A, and the at least another stress-generating material region such as the embedded source and drain regions (134, 234) can have the same material as the at least one stress-generating material region 34.

In a non-limiting illustrative example, the functional semiconductor device can be a field effect transistor, and the other single crystalline strained material region of which the strain is monitored can be a body region of the field effect transistor including a channel of the field effect transistor.

In one embodiment, the periodic array of unit structures is not contacted by any structure configured to apply electrical current through any portion of the periodic array of unit structures. At the same time, the functional semiconductor device can be contacted by at least one contact via structure configured to apply electrical current through the other single crystalline strained material region. For example, the functional semiconductor device can be contacted by at least one contact via structure 70, which can be electrically connected to at least one interconnect-level metal line 90 and at least one interconnect-level metal via 80.

While the present disclosure has been particularly shown and described with respect to preferred embodiments thereof, it will be understood by those skilled in the art that the foregoing and other changes in forms and details may be made without departing from the spirit and scope of the present disclosure. It is therefore intended that the present disclosure not be limited to the exact forms and details described and illustrated, but fall within the scope of the appended claims.

What is claimed is:

1. A method of measuring strain on a single crystalline structure generated by stress-generating elements, said method comprising:
    providing a periodic array of unit structures on a substrate, wherein each of said unit structures comprises a single crystalline strained material region and at least one stress-generating material region that applies stress to said single crystalline strained material region;
    performing a first X-ray scan on said periodic array of unit structures to generate an X-ray scan spectrum, wherein said first X-ray scan is performed before a processing step in a sequence of processing steps;
    locating a first Bragg peak of a material of said single crystalline strained material region in said X-ray scan spectrum;
    performing said processing step;
    performing a second X-ray scan on said periodic array of unit structures around said first Bragg peak of said material of said single crystalline strained material region to generate a second X-ray scan spectrum;
    locating a second Bragg peak of said material of said single crystalline strained material region in said second X-rag scan spectrum; and
    determining strain in a direction in said single crystalline strained material region in said periodic array of unit structures based on a difference in angle between said first Bragg peak and said second Bragg peak in said second X-ray scan spectrum.

2. The method of claim 1, wherein said single crystalline strained material region comprises a first single crystalline semiconductor material, and a single crystalline unstrained material region, wherein said single crystalline unstrained material region comprises said first single crystalline semiconductor material.

3. The method of claim 2, wherein said at least one stress-generating material region comprises a second single crystalline semiconductor material that is different from said first single crystalline semiconductor material.

4. The method of claim 3, wherein said second single crystalline semiconductor material is epitaxially grown on said first single crystalline semiconductor material in said unit structures.

5. The method of claim 3, wherein each of said unit structures further includes a single crystalline unstrained material region comprising said first single crystalline semiconductor material, and said second single crystalline semiconductor material in said at least one stress-generating material region is embedded in, and epitaxially aligned with, a contiguous portion of said first single crystalline semiconductor material including said single crystalline strained material region and said single crystalline unstrained material region.

6. The method of claim 3, wherein said first single crystalline semiconductor material is single crystalline silicon and said second single crystalline semiconductor material is a single crystalline alloy of silicon of at least one group IV element other than silicon.

7. The method of claim 6, wherein said at least one group IV element other than silicon is selected from germanium and carbon.

8. The method of claim 1, further comprising providing a semiconductor device on said substrate including another single crystalline strained material region and at least another stress-generating material region that applies stress to said other single crystalline strained material region, wherein said semiconductor device is configured to flow electrical current through said single crystalline strained material region.

9. The method of claim 8, wherein said other single crystalline strained material region has a same material as said single crystalline strained material region and said at least another stress-generating material region has the same material as said at least one stress-generating material region.

10. The method of claim 8, wherein said semiconductor device is a field effect transistor, and said other single crystalline strained material region is a body region of said field effect transistor including a channel of said field effect transistor.

11. The method of claim 8, wherein said periodic array of unit structures is not contacted by any structure configured to apply electrical current through any portion of said periodic array of unit structures.

12. The method of claim 11, wherein said semiconductor device is contacted by at least one contact via structure configured to apply electrical current through said other single crystalline strained material region.

13. The method of claim 1, wherein each of said unit structures includes a stack structure including a dielectric material portion and a conductive material portion, wherein said stack structure contacts and overlies said single crystalline strained material region, and said conductive material portion is encapsulated by said dielectric material portion and at least one dielectric material layer without contacting a conductive structure.

14. The method of claim 13, further comprising providing a field effect transistor on said substrate, said field effect transistor includes a gate dielectric having a same material composition and thickness as said dielectric material portion.

15. The method of claim 1, further comprising:
providing another periodic array of second unit structures on said substrate, said second unit structures differ from said unit structures by composition or volume of an element corresponding to said single crystalline strained material region or said at least one stress-generating material region; and
determining strain in said direction in additional single crystalline strained material regions in said other periodic array of second unit structures based on another X-ray scan spectrum generated from said other periodic array.

* * * * *